United States Patent
Iizuka et al.

(10) Patent No.: US 10,633,687 B2
(45) Date of Patent: *Apr. 28, 2020

(54) SUBSTRATE SOLUTION FOR MEASURING LIPASE ACTIVITY, AND METHOD AND REAGENT FOR MEASURING LIPASE ACTIVITY IN SAMPLE

(71) Applicant: Shino-Test Corporation, Tokyo (JP)

(72) Inventors: Naomi Iizuka, Sagamihara (JP); Atsushi Hikichi, Sagamihara (JP)

(73) Assignee: Shino-Test Corporation, Tokyo (JP)

( * ) Notice: Subject to any disclaimer, the term of this patent is extended or adjusted under 35 U.S.C. 154(b) by 3 days.

This patent is subject to a terminal disclaimer.

(21) Appl. No.: 15/737,856

(22) PCT Filed: Jun. 17, 2016

(86) PCT No.: PCT/JP2016/068116
§ 371 (c)(1),
(2) Date: Dec. 19, 2017

(87) PCT Pub. No.: WO2016/204276
PCT Pub. Date: Dec. 22, 2016

(65) Prior Publication Data
US 2018/0346961 A1 Dec. 6, 2018

(30) Foreign Application Priority Data

Jun. 19, 2015 (JP) ................................. 2015-124010

(51) Int. Cl.
| | | |
|---|---|---|
| *C12Q 1/44* | (2006.01) | |
| *C12N 9/20* | (2006.01) | |
| *C08G 77/14* | (2006.01) | |
| *G01N 33/92* | (2006.01) | |
| *C07D 265/38* | (2006.01) | |

(52) U.S. Cl.
CPC ............... *C12Q 1/44* (2013.01); *C08G 77/14* (2013.01); *C12N 9/20* (2013.01); *G01N 33/92* (2013.01); *C07D 265/38* (2013.01)

(58) Field of Classification Search
None
See application file for complete search history.

(56) References Cited

U.S. PATENT DOCUMENTS

| 4,847,376 A | 7/1989 | Neumann et al. |
|---|---|---|
| 2004/0053350 A1 | 3/2004 | Yamamoto et al. |
| 2008/0038765 A1 | 2/2008 | Imamura |
| 2009/0269323 A1* | 10/2009 | Luk ........................ A01N 25/04 424/94.3 |
| 2009/0269838 A1 | 10/2009 | Muraya |
| 2015/0151267 A1* | 6/2015 | Schmitt .................... A61K 8/11 424/401 |
| 2017/0152544 A1 | 6/2017 | Iizuka et al. |

FOREIGN PATENT DOCUMENTS

| JP | 58-156330 | 9/1983 |
|---|---|---|
| JP | 61-254197 | 11/1986 |
| JP | 9-154598 | 6/1997 |
| JP | 9-215500 | 8/1997 |
| JP | 11-318494 | 11/1999 |
| JP | 2002-214239 | 7/2002 |
| JP | 2007-306821 | 11/2007 |
| WO | 2006/054681 | 5/2006 |
| WO | 2006/092980 | 9/2006 |
| WO | 2016/024549 | 2/2016 |

OTHER PUBLICATIONS

Translation of Nonaka et al. (JP 09215500 A) published 1997; downloaded from the JPO on Mar. 17, 2019 (Year: 1997).*
Zelisko et al. Langmuir (2002) 18: 8982-8987 (Year: 2002).*
Definition of a solution downloaded from https://www.dictionary.com/browse/solition on Mar. 18, 2019 (Year: 2019).*
Kanai, Masamitsu, Kanai's Manual of Clinical Laboratory Medicine, 30th Edition, Published by Kanehara & Co., Ltd., on Aug. 20, 1993; pp. 670-674 (with partial English Translation).
Kanai, Masamitsu, Kanai's Manual of Clinical Laboratory Medicine, 33rd Edition, Published by Kanehara & Co., Ltd., on Apr. 1, 2010; pp. 545-547 (with partial English Translation).
Yoshinori, Uji, et al., Method of Serum Pancreatic Lipase Measurement Involving the Use of a Novel Substrate (resorufin), Journal of Biliary Tract & Pancreas, 2002, vol. 23, No. 6, pp. 455-459 (with partial English Translation).
International Search Report based on PCT International Application No. PCT/JP2016/068116, dated Sep. 20, 2016, 2 Pages.

* cited by examiner

*Primary Examiner* — Susan M Hanley
(74) *Attorney, Agent, or Firm* — McCarter & English, LLP

(57) ABSTRACT

This invention provides a substrate solution for measuring lipase activity, a reagent for measuring lipase activity, and an emulsion solution excellent in storage stability. This invention also provides a method for measuring lipase activity in a sample that enables accurate measurement over a long period of time. This invention further provides a method for improving storage stability of a substrate solution for measuring lipase activity and an emulsion solution. To this end, a substrate solution for measuring lipase activity comprising the emulsion solution comprising micelle particles of 1,2-o-dilauryl-rac-glycero-3-glutaric acid (6'-methylresorufin) ester and side-chain-type nonreactive polyether-modified-type modified silicone oil is used.

5 Claims, 12 Drawing Sheets

SUBSTRATE SOLUTION FOR MEASURING LIPASE ACTIVITY, AND METHOD AND REAGENT FOR MEASURING LIPASE ACTIVITY IN SAMPLE

RELATED APPLICATIONS

This application is a national stage application filed under 35 USC 371 of PCT/JP2016/068116, filed Jun. 17, 2016, which claims the benefit of Japanese Patent Application No. 2015-124010, filed Jun. 19, 2015, all of which is incorporated herein, in its entirety, by reference.

TECHNICAL FIELD

The present invention relates to a substrate solution for measuring lipase activity in a sample that is excellent in terms of storage stability.

The present invention also relates to a reagent for measuring lipase activity in a sample that is excellent in terms of storage stability.

The present invention also relates to a method for measuring lipase activity in a sample that can provide accurately measured values over a long period of time.

The present invention also relates to an emulsion solution comprising micelle particles of 1,2-o-dilauryl-rac-glycero-3-glutaric acid (6'-methylresorufin) ester and the like that is excellent in terms of storage stability.

The present invention also relates to a method for stabilizing a substrate solution for measuring lipase activity aimed at improving storage stability of a substrate solution for measuring lipase activity.

Also, the present invention relates to a method for stabilizing an emulsion solution comprising micelle particles of 1,2-o-dilauryl-rac-glycero-3-glutaric acid (6'-methylresorufin) ester and the like aimed at improving storage stability of the emulsion solution comprising micelle particles.

The present invention is useful in the field of, for example, life sciences such as clinical laboratory tests and chemistry, such as analytical chemistry.

Background Art

Lipase activity in serum or plasma is increased in pancreatic diseases (e.g., acute and chronic pancreatitis or pancreatic cancer), so that the lipase activity is a useful marker for the pancreatitis, etc.

The lipase is an enzyme that catalyzes a reaction in which ester bonds at α-positions (positions 1 and 3) of a triglyceride (TG) (three long-chain fatty acid molecules are each linked via an ester bond to glycerol) are hydrolyzed to produce two fatty acid molecules and one β-monoglyceride molecule.

This one β-monoglyceride molecule is isomerized to α-monoglyceride, which is then hydrolyzed by the lipase to produce glycerol and a fatty acid.

Examples of techniques for measuring lipase activity in serum or plasma include the following techniques (see Non-Patent Documents 1 and 2).

A known example is the Cherry-Crandall method in which an olive oil emulsion is used as a lipase substrate, this olive oil emulsion is made to contact and react with, for example, a serum sample at 37° C. for 24 hours, and then a fatty acid, which has been generated through hydrolysis by the lipase, is titrated with an alkali.

In this method, however, the reaction time is long, the lipase of interest can be inactivated, and the reaction is thus markedly inhibited.

Another known example is the Vogel-Zieve method and a modified method thereof in which a triolein or olive oil emulsion is used as a lipase substrate, this triolein or olive oil emulsion is made to contact and react with, for example, a serum sample, the emulsified micelles are then hydrolyzed by the lipase to cause a decrease in turbidity of the resulting reaction solution, and the lipase activity is determined on the basis of the decrease.

These methods, however, involve serum protein-mediated inhibition and/or interference due to rheumatoid factor-induced aggregation, so that it is difficult to produce a uniform and stable emulsion. Also, the methods are poorly reproducible and thus disadvantageous.

Another known example is a technique for measuring lipase activity in which BALB (2,3-dimercapto-1-propanol tributyrate) is used as a lipase substrate, this BALB is made to contact and react with, for example, a serum sample, BAL (2,3-dimercapto-1-propanol), which has been generated through hydrolysis by the lipase, is reacted with DTNB (5,5'-dithiobis-2-nitrobenzoic acid), and yellow light emitted by the resulting TNB anion is measured at 412 nm.

This measurement, however, involves interference with a liver esterase under highly concentrated conditions. Accordingly, the liver esterase is mixed through a reaction cell or a nozzle (probe) from a reagent for measuring another item. This affects a measured value and causes an error, so that this measurement is disadvantageous.

Another known example is a technique for measuring lipase activity in which 1,2-dilinoleoyl glycerol, which is a natural substrate, is used as a lipase substrate, this 1,2-dilinoleoyl glycerol is made to contact and react with, for example, a serum sample, linoleic acid, which has been generated through hydrolysis by the lipase, cooperates, in the presence of Coenzyme A, $NAD^+$, and ATP, with acyl-CoA synthetase, Acyl-CoA oxidase, and an enoyl-CoA hydratase-3-hydroxyacyl-CoA dehydrogenase-3-ketoacyl-CoA thiolase multienzyme complex to perform β-oxidation, and the NADH production rate when the β-oxidation occurs is then measured.

This measurement, however, also involves interference with a liver esterase under highly concentrated conditions. Accordingly, the liver esterase is mixed through a reaction cell or a nozzle (probe) from a reagent for measuring another item. This affects a measured value and causes an error, so that this measurement is disadvantageous.

In addition to the above respective measurements, a technique for measuring lipase activity in serum or plasma has been developed in which 1,2-o-dilauryl-rac-glycero-3-glutaric acid (6'-methylresorufin) ester (hereafter, sometimes referred to as "DGGMR") is used as a lipase substrate (see Patent Document 1 and Non-Patent Document 2).

In this measurement, 1,2-o-dilauryl-rac-glycero-3-glutaric acid (6'-methylresorufin) ester (DGGMR) is made to contact and react with, for example, a serum sample, and the lipase catalyzes hydrolysis to generate 1,2-o-dilauryl-rac-glycerol and glutaric acid (6'-methylresorufin) ester.

This glutaric acid (6'-methylresorufin) ester is unstable and is hydrolyzed readily and naturally to generate 6'-methylresorufin (λmax: 580 nm).

An increase in the 6'-methylresorufin generated is measured by reading the absorbance at or near 580 nm. Thus, the lipase activity value in the sample can be determined.

This technique for measuring lipase activity using DGGMR as a lipase substrate is simple because the measurement proceeds in a series of reactions. Besides, the measurement is also advantageous because the measurement is unlikely to be affected by an esterase mixed through a reaction cell or a nozzle (probe) from other measuring reagents.

Meanwhile, a lipase contained in, for example, serum or plasma is most efficient at a water-oil interface of an emulsified triglyceride substrate. The reaction rate of this lipase involves the surface area of the substrate dispersed. To measure the lipase activity, accordingly, it seems critical to prepare a substrate composed of stable and uniform micelle particles (see Non-Patent Document 2).

For this purpose, when a substrate solution for measuring lipase activity (i.e., a substrate solution for lipase activity measurement) is produced conventionally, the substrate solution should be emulsified and composed of stable and uniform micelle particles. To this end, various methods have been taken into consideration. For example, a substrate may be mixed into an aqueous solution containing a surfactant, a substrate may be mixed into a solution containing an organic solvent (e.g., an alcohol), a substrate-containing liquid may be added dropwise and mixed into a solution, a substrate-containing liquid may be jet-injected into a solution, a substrate solution may be stirred with a powerful mixer at a high speed, or a substrate solution may be subject to ultrasonication. The methods necessitate complicated or special processing such that skill is required. The methods also necessitate a special apparatus, instruments, or other items.

In general, a solution containing a substrate for measuring lipase activity is unstable, and it is problematic in terms of its storage stability.

In order to improve storage stability of a solution containing a substrate for measuring lipase activity, accordingly, various attempts have been made.

For example, a process for producing a transparent miscible aqueous solution containing a water-insoluble substance characterized in that a water-insoluble substance (e.g., triglyceride) as a lipase substrate is added to an aqueous solution containing a nonionic surfactant, the mixture is heated while being stirred, the temperature is once raised to a temperature higher than the cloud point of the nonionic surfactant, and the temperature is then cooled to a temperature equal to or lower than the cloud point while the mixture is further stirred was disclosed as a process that would make a water-insoluble substance miscible, which was difficult in the past, and the miscible aqueous solution obtained by such process is very stable (see Patent Document 2).

In addition, a diglyceride solution for measuring lipase activity comprising a low-concentration pH buffer solution and a nonionic surfactant, such as a polyoxyethylene alkyl phenyl ether nonionic surfactant was disclosed as a substance that would enable provision of an aqueous solution of diglyceride exhibiting long-term storage stability (see Patent Document 3).

Further, a composition for measuring plant- and/or microbe-derived lipase activity characterized by the use of diglyceride, as a substance, dissolved in a nonionic surfactant, such as a polyoxyethylene alkyl phenyl ether nonionic surfactant, was disclosed that would enable provision of a kit and a composition containing an aqueous diglyceride solution excellent in long-term storage stability (see Patent Document 4).

Furthermore, a lipase substrate solution for measuring enzyme activity, which was made soluble in a lipase substrate comprising DGGMR or the like by a novel lipase substrate solubilizer (i.e., 1,2-diphytanoyl-sn-glycero-3-phosphocholine), was disclosed as a substance that would enable enhanced storage stability and an increased degree of transparency for a long period of time (see Patent Document 5).

PRIOR ART DOCUMENTS

Patent Documents

Patent Document 1: JP Patent Publication (Kokai) No. S61-254197A (1986)
Patent Document 2: JP Patent Publication (Kokai) No. S58-156330A (1983)
Patent Document 3: WO 2006/054681
Patent Document 4: JP Patent Publication (Kokai) No. 2007-306821 A
Patent Document 5: JP Patent Publication (Kokai) No. H11-318494 A (1999)

Non-Patent Documents

Non-Patent Document 1: Kanai's Manual of Clinical Laboratory Medicine, 30th ed., p. 670-674, edited by KANAI, Masamitsu, published by KANEHARA & Co., Ltd., on Aug. 20, 1993.
Non-Patent Document 2: Kanai's Manual of Clinical Laboratory Medicine, 33th ed., p. 545-547, edited by KANAI. Masamitsu, published by KANEHARA & Co., Ltd., on Apr. 1, 2010.

SUMMARY OF INVENTION

Objects to be Attained by the Invention

As described above, Patent Document 5 describes that a lipase substrate solution for measuring enzyme activity comprising DGGMR as a substrate for measuring lipase activity in combination with a novel lipase substrate solubilizer (i.e., 1,2-diphytanoyl-sn-glycero-3-phosphocholine) exhibits high storage stability. However, 1,2-diphytanoyl-sn-glycero-3-phosphocholine is expensive and, accordingly, a cost for a raw material of the substrate solution is disadvantageously increased.

In contrast, the present invention is intended to provide a substrate solution for measuring lipase activity comprising DGGMR having various advantages when used as a substrate for measuring lipase activity as a substrate for measuring lipase activity as described above, which is excellent in terms of storage stability.

Also, the present invention is intended to provide a reagent for measuring lipase activity comprising a substrate solution for measuring lipase activity comprising DGGMR as a substrate for measuring lipase activity, which is excellent in terms of storage stability.

Also, the present invention is intended to provide a method for measuring lipase activity in a sample involving the use of a substrate solution for measuring lipase activity comprising DGGMR as a substrate for measuring lipase activity, which can provide accurately measured values over a long period of time.

Also, the present invention is intended to provide an emulsion solution comprising micelle particles of DGGMR and the like, which is excellent in terms of storage stability.

Also, the present invention is intended to provide a method for stabilizing a substrate solution for measuring lipase activity that improves storage stability of the substrate solution for measuring lipase activity.

Also, the present invention is intended to provide a method for stabilizing an emulsion solution comprising micelle particles of DGGMR and the like that improves storage stability of the emulsion solution comprising micelle particles.

Means for Attaining the Objects

The present inventors have conducted concentrated studies concerning a method for improving storage stability of a substrate solution for measuring lipase activity comprising DGGMR as a substrate for measuring lipase activity, a method for stabilizing an emulsion solution comprising micelle particles of DGGMR, and the like. As a result, they discovered that the objects of the present invention could be achieved by incorporating DGGMR in combination with side-chain-type nonreactive polyether-modified-type modified silicone oil into the solution. This has led to the completion of the present invention.

The present invention is summarized as follows.

[1] A substrate solution for measuring lipase activity composed of an emulsion solution comprising micelle particles of 1,2-o-dilauryl-rac-glycero-3-glutaric acid (6'-methylresorufin) ester and side-chain-type nonreactive polyether-modified-type modified silicone oil.

[2] A reagent for measuring lipase activity comprising a substrate solution for measuring lipase activity composed of an emulsion solution comprising micelle particles of 1,2-o-dilauryl-rac-glycero-3-glutaric acid (6'-methylresorufin) ester and side-chain-type nonreactive polyether-modified-type modified silicone oil.

[3] A method for measuring lipase activity in a sample with the use of a substrate solution for measuring lipase activity composed of an emulsion solution comprising micelle particles of 1,2-o-dilauryl-rac-glycero-3-glutaric acid (6'-methylresorufin) ester and side-chain-type nonreactive polyether-modified-type modified silicone oil.

[4] An emulsion solution comprising micelle particles of 1,2-o-dilauryl-rac-glycero-3-glutaric acid (6'-methylresorufin) ester and side-chain-type nonreactive polyether-modified-type modified silicone oil.

[5] A method for stabilizing a substrate solution for measuring lipase activity involving the use of 1,2-o-dilauryl-rac-glycero-3-glutaric acid (6'-methylresorufin) ester as a substrate for measuring lipase activity comprising: containing side-chain-type nonreactive polyether-modified-type modified silicone oil together with 1,2-o-dilauryl-rac-glycero-3-glutaric acid (6'-methylresorufin) ester.

[6] A method for stabilizing an emulsion solution comprising micelle particles of 1,2-o-dilauryl-rac-glycero-3-glutaric acid (6'-methylresorufin) ester comprising: containing side-chain-type nonreactive polyether-modified-type modified silicone oil together with 1,2-o-dilauryl-rac-glycero-3-glutaric acid (6'-methylresorufin) ester.

Effects of the Invention

The substrate solution for measuring lipase activity of the present invention is excellent in terms of storage stability.

The reagent for measuring lipase activity of the present invention is excellent in terms of storage stability.

The method for measuring lipase activity in a sample of the present invention can provide accurately measured values over a long period of time.

The emulsion solution comprising micelle particles of DGGMR and the like of the present invention is excellent in terms of storage stability.

The method for stabilizing the substrate solution for measuring lipase activity of the present invention is capable of improving storage stability of the substrate solution for measuring lipase activity.

The method for stabilizing the emulsion solution comprising micelle particles of DGGMR and the like of the present invention is capable of improving storage stability of the emulsion solution.

As described above, the substrate solution for measuring lipase activity, the reagent for measuring lipase activity, and the emulsion solution of the present invention and the methods of the present invention enable the stable use of a substrate solution for measuring lipase activity comprising DGGMR as a substrate for measuring lipase activity, the reagent for measuring lipase activity comprising the substrate solution for measuring lipase activity, and the emulsion solution comprising micelle particles of DGGMR and the like for a long period of time. Thus, the present invention is convenient for the users and is advantageous in respect of the cost.

As described above, the substrate solution for measuring lipase activity, the reagent for measuring lipase activity, and the emulsion solution of the present invention enable the stable use of the substrate solution for measuring lipase activity comprising DGGMR as a substrate for measuring lipase activity, a reagent for measuring lipase activity comprising the substrate solution for measuring lipase activity, and an emulsion solution comprising micelle particles of DGGMR and the like over a long period of time. Accordingly, a substrate solution for measuring lipase activity that provides accurate results of measurement (the measured value) over a long period of time and a reagent for measuring lipase activity comprising such substrate solution became available for medical institutions and the like. At medical institutions and the like, accordingly, accurate results of measurement (the measured value) of lipase activity in a sample became obtainable over a long period of time.

EMBODIMENTS FOR CARRYING OUT THE INVENTION

Figure 1:
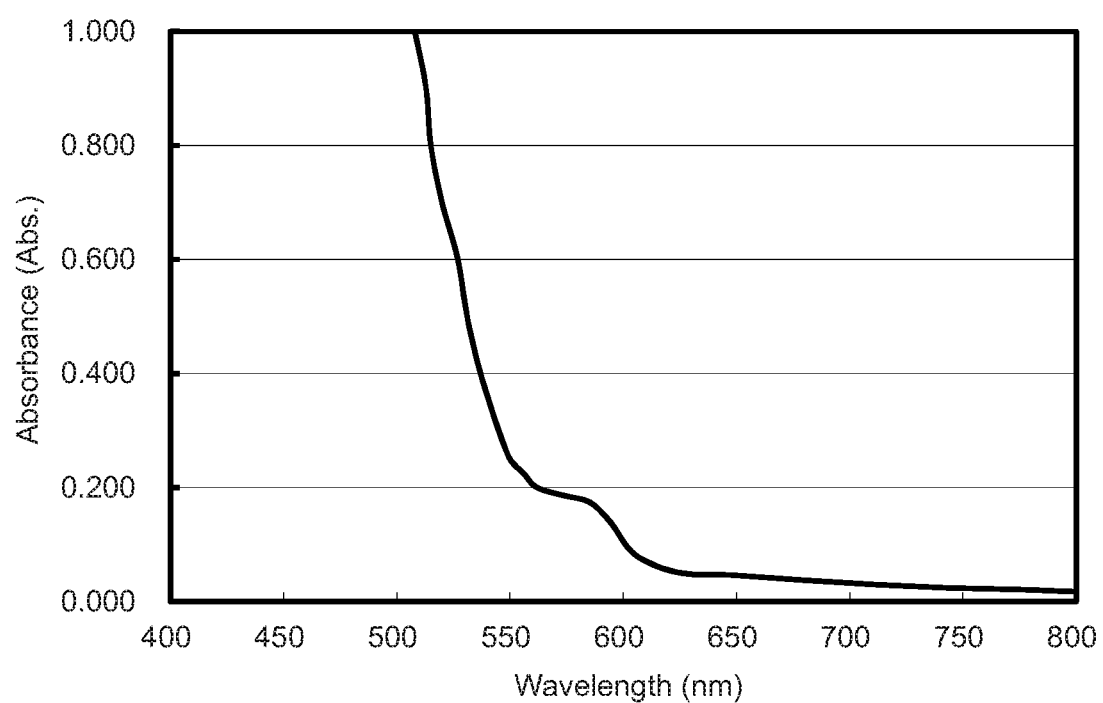
FIG. 1 shows an absorption curve of a mixture using the stored substrate solution for measuring lipase activity of the present invention.

[1] Substrate Solution for Measuring Lipase Activity of the Present Invention

I. Overview

1. Substrate Solution for Measuring Lipase Activity

The substrate solution for measuring lipase activity of the present invention is composed of an emulsion solution comprising micelle particles of 1,2-o-dilauryl-rac-glycero-3-glutaric acid (6'-methylresorufin) ester (DGGMR) and side-chain-type nonreactive polyether-modified-type modified silicone oil.

Because of such composition, the substrate solution for measuring lipase activity of the present invention is excellent in terms of storage stability.

2. Lipase

In the present invention, a lipase should have activity as a lipase; that is, it should have lipase activity. The lipase is not particularly limited as long as it has the lipase activity.

In the present invention, examples of the lipase include a pancreatic lipase (EC 3.1.1.3) that catalyzes a reaction in which ester bonds at α-positions (positions 1 and 3) of a triglyceride (TG) (three long-chain fatty acid molecules are each linked via an ester bond to glycerol) are hydrolyzed to produce two fatty acid molecules and one β-monoglyceride molecule.

The present invention is preferable for measuring the activity of a lipase present in body fluid, an organ, or a tissue, more preferable for measuring the activity of a lipase present in body fluid, still more preferable for measuring the activity of a lipase present in blood, serum, or plasma, and furthermore preferable for measuring the activity of a lipase present in serum or plasma.

In addition, the present invention is suitable for measuring the activity of a pancreatic lipase.

3. Sample

In the present invention, a sample for measuring lipase activity may be a sample that can contain the above lipase. The sample is not particularly limited as long as the sample can contain the above lipase.

Examples of samples include human-, animal-, and plant-derived samples.

Examples of human- and animal-derived samples include, but are not particularly limited to, human or animal body fluid (e.g., blood, serum, plasma, urine, semen, spinal fluid, saliva, sweat, teardrops, ascites, or amnion liquid), excrement (e.g., feces), organs (e.g., a pancreas, liver, or stomach), tissues (e.g., a hair, skin, nail, muscle, or nerve), and cells.

The present invention is suitable when the human- or animal-derived sample is used as a sample and more suitable when the human-derived sample is used as a sample.

In addition, the present invention is preferable when the body fluid, organ, or tissue is used as a sample, more preferable when the body fluid is used as a sample, still more preferable when the blood, serum, or plasma is used as a sample, and furthermore preferable when the serum or plasma is used as a sample.

Note that, in the present invention, a liquid sample is preferable. So, if the sample is not liquid, pretreatment (e.g., extraction or solubilization) may be performed in accordance with a known procedure to prepare a liquid sample.

In addition, the sample may be diluted or enriched as needed.

II. Emulsion Solution of the Present Invention

I. Overview

As described above, the substrate solution for measuring lipase activity of the present invention comprises an emulsion solution comprising micelle particles of 1,2-o-dilauryl-rac-glycero-3-glutaric acid (6'-methylresorufin) ester and side-chain-type nonreactive polyether-modified-type modified silicone oil.

The emulsion solution comprising micelle particles of 1,2-o-dilauryl-rac-glycero-3-glutaric acid (6'-methylresorufin) ester and side-chain-type nonreactive polyether-modified-type modified silicone oil of the present invention is described below.

The emulsion solution of the present invention (i.e., the emulsion solution comprising micelle particles of 1,2-o-dilauryl-rac-glycero-3-glutaric acid (6'-methylresorufin) ester and side-chain-type nonreactive polyether-modified-type modified silicone oil) may comprise substances other than 1,2-o-dilauryl-rac-glycero-3-glutaric acid (6'-methylresorufin) ester and side-chain-type nonreactive polyether-modified-type modified silicone oil, as described below.

2. Substrate for Measuring Lipase Activity (1) Overview

In the present invention, a lipase substrate for measuring lipase activity in a sample; that is, a substrate for measuring lipase activity, is 1,2-o-dilauryl-rac-glycero-3-glutaric acid (6'-methylresorufin) ester (DGGMR).

In the present invention, DGGMR, which is a substrate for measuring lipase activity, is brought into contact with a sample and is then allowed to react with a lipase contained in the sample. Thus, 1,2-o-dilauryl-rac-glycerol and glutaric acid (6'-methylresorufin) ester are generated from DGGMR as a result of hydrolysis catalyzed by the lipase.

This glutaric acid (6'-methylresorufin) ester is unstable and is hydrolyzed readily and naturally to generate 6'-methylresorufin ($\lambda$max: 580 nm).

In the present invention, an increase in the 6'-methylresorufin generated is measured by reading the absorbance at or near 580 run. Thus, the lipase activity value in the sample can be determined.

DGGMR is commercially available from, for example, Roche Diagnostics K. K. (Japan) or Sigma-Aldrich Co. LLC. (Japan).

(2) Concentration of Substrate for Measuring Lipase Activity

The concentration of DGGMR in the emulsion solution of the present invention is preferably 0.05 mM or higher in order to obtain an emulsion solution composed of stable and uniform micelle particles.

The concentration of DGGMR in the emulsion solution of the present invention is more preferably 0.1 mM or higher, and still more preferably 0.2 mM or higher in view of the above purpose.

The concentration of DGGMR contained in the emulsion solution of the present invention is 2 mM or lower in view of the above purpose.

The concentration of DGGMR in the emulsion solution of the present invention is more preferably 1 mM or lower, and still more preferably 0.8 mM or lower in view of the above purpose.

2. Modified Silicone Oil of the Present Invention (1) Overview

As described above, the substrate solution for measuring lipase activity of the present invention is composed of an emulsion solution comprising micelle particles of DGGMR as a substrate for measuring lipase activity and side-chain-type nonreactive polyether-modified-type modified silicone oil.

Specifically, the emulsion solution of the present invention comprises DGGMR in combination with side-chain-type nonreactive polyether-modified-type modified silicone oil.

(2) Side-Chain-Type Nonreactive Polyether-Modified-Type Modified Silicone Oil

The side-chain-type nonreactive polyether-modified-type modified silicone oil used in the present invention (hereafter, occasionally referred to as "the present modified silicone oil") is described below.

The silicone compound is a polymer compound containing, as a main chain, a siloxane linkage (—Si—O—Si—) and, as a side chain, an organic group (e.g., a methyl group ($CH_3$—)) bonded to a silicon atom.

Here, a linear silicone compound is silicone oil.

The modified silicone oil is a compound in which an organic group is introduced into a portion of silicon atoms of a linear dimethyl silicone compound "$Si(CH_3)_3$—O—[$Si(CH_3)_2$—O-]m-$Si(CH_3)_3$".

Examples of the modified silicone oil include silicone oils in which various organic groups are introduced into a part of side chains of polysiloxane, either end of polysiloxane, both ends of polysiloxane, and a part of side chains and both ends of polysiloxane.

Among them, the silicone oil in which various organic groups are introduced into a part of side chains of polysiloxane is side-chain-type modified silicone oil "$Si(CH_3)_3$—O—[$Si(CH_3)_2$—O-]m-[$Si(CH_3)$(an organic group)-O-]n-$Si(CH_3)_3$."

Depending on characteristics of the organic groups to be introduced, the modified silicone oils are classified into reactive silicone oil and nonreactive silicone oil.

Depending on the organic group to be introduced, examples of the nonreactive modified silicone oil include polyether modified type, aralkyl modified type, fluoroalkyl modified type, long-chain alkyl modified type, higher fatty acid ester modified type, higher fatty acid amide modified type, polyether/long-chain alkyl/aralkyl modified type, long-chain alkyl/aralkyl modified type, and phenyl modified type silicone oil.

As the side-chain-type nonreactive modified silicone oil "Si—$(CH_3)_3$—O—[$Si(CH_3)_2$—O-]m-[$Si(CH_3)$(an organic group)-O-]n-$Si(CH_3)_3$," examples of the modified type silicone oil include a polyether modified type silicone oil (the organic group: —$R(C_2H_4O)_a(C_3H_6O)_bR'$), a polyether/long-chain alky/aralkyl modified type silicone oil (the organic group: —$R(C_2H_4O)_n(C_3H_6O)_bR'$, —$C_8H_{2a+1}$, —$CH_2$—$CH(CH_3)$—$C_6H_5$), an aralkyl modified type silicone oil (the organic group: —$CH_2$—$CH(CH_3)$—$C_6H_5$), a fluoroalkyl modified type silicone oil (the organic group: —$CH_2CH_2CF_3$), a long-chain alkyl modified type silicone oil (the organic group: —$C_aH_{2a+1}$), a long-chain alkyl/aralkyl modified type silicone oil (the organic group: —$C_aH_{2a+1}$, —$CH_2$—$CH(CH_3)$—$C_6H_5$), a higher fatty acid ester modified type silicone oil (the organic group: —OCOR), a higher fatty acid amide modified type silicone oil (the organic group: —RNHCOR'), and a phenyl modified type silicone oil (the organic group: —$C_6H_5$).

In the present invention, the side-chain-type nonreactive polyether-modified-type modified silicone oil ($Si(CH_3)_3$—O—[$Si(CH_3)_2$—O-]m-[$Si(CH_3)$(an organic group)-(O-]n-$Si(CH_3)_3$) (an organic group: —$R(C_2H_4O)_a(C_3H_6O)_nR'$)) is used.

Examples of commercially available side-chain-type nonreactive polyether-modified-type modified silicone oil include "KF-351A," "KF-354L," "KF-355A," and "KF-6011" (the distributor of the above products is Shin-Etsu Chemical Co., Ltd. (Japan)).

(3) Concentration of the Present Modified Silicone Oil

The concentration of the present modified silicone oil in the emulsion solution of the present invention is preferably 0.01% (w/v) or higher so as to prepare an emulsion solution composed of stable and uniform micelle particles.

The concentration of the present modified silicone oil in the emulsion solution of the present invention is more preferably 0.05% (w/v) or higher, and still more preferably 0.1% (w/v) or higher in view of the above purpose.

The concentration of the present modified silicone oil to be contained in the emulsion solution of the present invention is preferably 20% (w/v) or lower in view of the above purpose.

The concentration of the present modified silicone oil in the emulsion solution of the present invention is more preferably 10% (w/v) or lower, and still more preferably 5% (w/v) or lower in view of the above purpose.

3. Lipase Promoter (1) Lipase Promoter

The emulsion solution of the present invention may comprise a lipase promoter.

In the present invention, any substance may be used as a lipase promoter, provided that such substance can promote lipase activity. Examples include, but are not particularly limited to, bile acid and a salt thereof.

Examples of the bile acid include deoxycholic acid, taurodeoxycholic acid, glycodeoxycholic acid, cholic acid, lithocholic acid, glycocholic acid, taurocholic acid, chenodeoxycholic acid, ursodeoxycholic acid, 7-oxolithocholic acid, 12-oxolithocholic acid, 12-oxochenodeoxycholic acid, 7-oxodeoxycholic acid, hyocholic acid, hyodeoxycholic acid, dehydrocholic acid, and cholic acid derivatives.

In addition, examples of a salt of the bile acid include alkali metal or alkaline-earth metal salts of bile acid and an ammonium salt of bile acid.

Examples of the alkali metal include potassium, sodium, and lithium. In addition, examples of the alkaline-earth metal include magnesium and calcium.

As the lipase promoter, bile acid or a salt thereof is preferable because of their lipase activity-promoting function, an ability to form an interface composed of a substrate for measuring lipase activity, water solubility, and cost.

As the bile acid, taurodeoxycholic acid is preferable because it is soluble in an acidic range within which a substrate for measuring lipase activity (DGGMR) is stable. In view of cost, deoxycholic acid is preferable.

As the bile acid, taurodeoxycholic acid is more preferable.

As a salt of the bile acid, an alkali metal salt of the bile acid is preferable, a potassium or sodium salt of the bile acid is more preferable, and a sodium salt of the bile acid is still more preferable.

Thus, as a salt of the bile acid, an alkali metal (e.g., potassium or sodium) salt of deoxycholic acid or taurodeoxycholic acid is preferable, an alkali metal (e.g., potassium or sodium) salt of taurodeoxycholic acid is more preferable, and a sodium salt of taurodeoxycholic acid is still more preferable.

(2) Concentration of Lipase Promoter

The concentration of the lipase promoter in the emulsion solution of the present invention is preferably 0.2% (w/v) or higher.

The concentration of the lipase promoter in the emulsion solution of the present invention is more preferably 0.4% (w/v) or higher, and still more preferably 1% (w/v) or higher.

The concentration of the lipase promoter in the emulsion solution of the present invention is preferably 20% (w/v) or less.

The concentration of the lipase promoter in the emulsion solution of the present invention is more preferably 10% (w/v) or less and still more preferably 5% (w/v) or less.

4. Lipase Activator (1) Lipase Activator

The emulsion solution of the present invention may comprise a lipase activator.

In the present invention, the lipase activator may be any substance, provided that it can activate a lipase. Examples thereof include, but are not particularly limited to, an ion or salt of an alkaline-earth metal.

Examples of the ion or salt of an alkaline-earth metal include a beryllium ion or beryllium salt, a magnesium ion or magnesium salt, and a calcium ion or calcium salt.

Examples of the calcium salt include a water-soluble calcium salt. Specific examples thereof include a water-soluble salt containing a monovalent or divalent or higher anion and a calcium ion.

Examples of the anion include a halogen ion, an acid group of an organic compound, and an acid group of another inorganic compound.

Examples of the halogen ion include a fluorine ion and a chlorine ion.

Examples of the acid group of an organic compound include an acetate ion, a citrate ion, and a gluconate ion.

Examples of the acid group of an inorganic compound include a sulfate ion, a phosphate ion, and a carbonate ion.

The lipase activator is preferably an ion or salt of an alkaline-earth metal.

As the ion or salt of an alkaline-earth metal, a calcium ion or a calcium salt is preferable in view of the following points (i) and (ii):

(i) the ability to activate a lipase; and (ii) a fatty acid that is released from a substrate for measuring lipase activity while the lipase exerts its catalytic activity disrupts an interface composed of the substrate for measuring lipase activity, but a calcium ion or a calcium salt can capture the released fatty acid, thereby preventing the interface from being disrupted.

As the calcium salt, a water-soluble calcium salt containing an anion and a calcium ion is preferable.

The anion is preferably a halogen ion or an acid group of an organic compound. More specifically, a chlorine ion or an acetate ion is particularly preferable.

As the calcium salt, accordingly, a calcium halide or a calcium salt of an acid group of an organic compound is preferable, and calcium chloride or calcium acetate is more preferable.

(2) Concentration of Lipase Activator

The concentration of the lipase activator in the emulsion solution of the present invention is preferably 0.1 mM or higher.

The concentration of the lipase activator in the emulsion solution of the present invention is more preferably 1 mM or higher and still more preferably 5 mM or higher.

The concentration of the lipase activator in the emulsion solution of the present invention is preferably 100 mM or lower.

The concentration of the lipase activator in the emulsion solution of the present invention is more preferably 50 mM or lower and still more preferably 25 mM or lower.

5. Colipase (1) Colipase

The emulsion solution of the present invention may comprise a colipase.

In the present invention, a colipase is not particularly limited, provided that it has the effect, function, or activity of a colipase. Examples thereof include colipases derived from mammals (e.g., a human or pig) and colipases prepared, modified, or altered via genetic engineering.

A colipase derived from a mammal (e.g., a pig) is preferable, and a colipase derived from the pancreas of a mammal (e.g., a pig) is more preferable.

(2) Activity Value of Colipase

The activity value of the colipase in the emulsion solution of the present invention is preferably 15K Unit/L or higher.

The activity value of the colipase in the emulsion solution of the present invention is more preferably 150K Unit/L or higher and still more preferably 750K Unit/L or higher.

The activity value of the colipase in the emulsion solution of the present invention is preferably 7,500K Unit/L or lower.

The activity value of the colipase in the emulsion solution of the present invention is more preferably 3,750K Unit/L or lower and still more preferably 2,250K Unit/L or lower.

In the description and the drawings of the present application, each activity value (Unit/L) of the colipase is based on the indication of the activity value of a porcine pancreas-derived colipase (Roche Diagnostics K. K. (Japan)) (1 mg/L=75K Unit/L).

The colipase is commercially available from, for example, Roche Diagnostics K. K. (Japan) or Sigma-Aldrich Co. LLC. (Japan).

6. Water

The emulsion solution of the present invention may comprise water.

Specifically, the emulsion solution of the present invention may be an aqueous solution.

Water to be contained in the emulsion solution of the present invention is not particularly limited. Examples of water include pure water, distilled water, and purified water.

7. pH

The substrate for measuring lipase activity (DGGMR) according to the present invention is stable at or near pH 4.

Thus, the pH of the emulsion solution of the present invention is preferably within a certain range relative to pH 4.

In view of stability of DGGMR, specifically, the pH of the emulsion solution of the present invention is preferably from 2 to 7, more preferably from 3 to 5, and still more preferably from 3.5 to 4.5 (the pH values are measured at 20° C.).

8. Buffer (1) Buffer

The emulsion solution of the present invention may comprise a buffer.

In the present invention, the emulsion solution of the present invention may comprise a buffer with buffering capability within the pH1 range described in 7, above, according to need, so as to adjust the pH1 level of the emulsion solution of the present invention within the pH range described in 7, above.

Examples of buffers that can be contained in the emulsion solution of the present invention include, but are not particularly limited to, organic acids (e.g., tartaric acid, succinic acid, malonic acid, and citric acid), glycine, phosphoric acid, and salts thereof.

(2) Concentration of Buffer

In the present invention, the concentration of the butter to be contained in the emulsion solution of the present invention is not particularly limited, provided that the buffering capability can be exerted within a prescribed pH range.

For example, the concentration of the buffer in the emulsion solution of the present invention is preferably 5 mM or higher, more preferably 10 mM or higher, and still more preferably 30 mM or higher.

The concentration of the buffer in the emulsion solution of the present invention is preferably 500 mM or lower, more preferably 100 mM or lower, and particularly preferably 50 mM or lower.

9. Diameter of Micelles in the Emulsion Solution of the Present Invention

As described above, a lipase acts most effectively in a water-oil interface of an emulsified triglyceride substrate. The reaction rate of the lipase is associated with the surface area of the substrate dispersed. Thus, preparation of a substrate composed of stable and uniform micelle particles seems critical for measuring the lipase activity (see Non Patent Document 2).

In the present invention, it is preferable that the diameter (particle size) of micelles in the emulsion solution containing a substrate for measuring lipase activity (DGGMR) be within a range from 60 to 1.500 nm, so that the rate for the reaction with the lipase is high, the emulsion is stable, and the emulsion solution of the present invention can be stored and used for a long period of time.

For this reason, the diameter (particle size) of micelles in the emulsion solution of the present invention is more preferably from 70 to 1,000 nm, still more preferably from 80 to 600 nm, and further more preferably from 10 to 200 nm.

III. Process for Producing the Emulsion Solution of the Present Invention

1. Overview

A process for producing the emulsion solution of the present invention is not particularly limited, provided that the emulsion solution of the present invention "comprising micelle particles of DGGMR and the present modified silicone oil" can be produced by such process.

An example of a process for producing the emulsion solution of the present invention is a process comprising of steps (a) and (b) described below. In the present invention, the "process comprising of steps (a) and (b) described below" encompasses the "process comprising steps (a) and (b) described below."

The process comprising of steps (a) and (b) is preferable since the emulsion solution of the present invention can be produced without complicated or special processing such that skill is required or without the use of a special apparatus, instruments, or other items:

(a) a step of mixing DGGMR with the present modified silicone oil to prepare a mixture; and (b) a step of mixing all or a portion of the mixture prepared in step (a) with water or an aqueous solution.

2. Step of Mixing DGGMR with the Present Modified Silicone Oil to Prepare a Mixture Hereafter, the step (a) in 1, described above; i.e., "a step of mixing DGGMR with the present modified silicone oil to prepare a mixture" is described in detail.

(1) Mixing DGGMR with Modified Silicone Oil

In the step (a) in 1; that is, the step of mixing DGGMR with the present modified silicone oil to prepare a mixture, DGGMR, which is a substrate for measuring lipase activity, is mixed with the present modified silicone oil.

Specifically, DGGMR is mixed directly with the present modified silicone oil.

A single type of the present modified silicone oil or a plurality of types thereof may be mixed with DGGMR.

(2) Amount of DGGMR Mixed

In the step of mixing DGGMR as a substrate for measuring lipase activity with the present modified silicone oil to prepare a mixture, the amount of DGGMR to be mixed is not particularly limited.

The concentration of DGGMR is preferably 0.05 mM or higher after the step (b) in 1, above (i.e., the step of mixing "all or a portion of the mixture of DGGMR and the present modified silicone oil" with "water or an aqueous solution") (hereinafter, occasionally referred to as the "second mixing") for the purpose of producing an emulsion solution composed of stable and uniform micelle particles.

After the second mixing, the concentration of DGGMR is more preferably 0.1 mM or higher and still more preferably 0.2 mM or higher in view of the above purpose.

After the second mixing, the concentration of DGGMR is preferably 2 mM or lower in view of the above purpose.

After the second mixing, the concentration of DGGMR is more preferably 1 mM or lower and still more preferably 0.8 mM or lower in view of the above purpose.

The preferable concentration of DGGMR after the second mixing is as described above.

In the step (a) in 1. described above (i.e., the step of mixing DGGMR with the present modified silicone oil to prepare a mixture") (hereafter, occasionally referred to as "first mixing"), the amount of the DGGMR and that of the present modified silicone oil to be mixed with each other may adequately be determined, so as to adjust the concentration of DGGMR to the level described above after the second mixing. This is preferable in light of the production procedure.

Regarding the amount of DGGMR mixed and the concentration thereof, for example, the following cases (a) and (b) may be considered.

(a) Case where all of the Mixture of the Substrate for Measuring Lipase Activity and the Present Modified Silicone Oil is Mixed with Water or an Aqueous Solution The amount of the substrate for measuring lipase activity mixed at the time of the first mixing is set to Ws (represented in gram). The final volume (e.g., the volume adjusted to the designated level) after water or an aqueous solution is mixed at the time of the second mixing is set to Vf (represented in mL). The molecular weight of the substrate for measuring lipase activity is set to MWs. The concentration Cs (represented in mM) of the substrate for measuring lipase activity after the second mixing can be expressed by the following equation.

$$Cs=(Ws\times10)/(Vf\times MWs).$$

Since the molecular weight MWs of the substrate for measuring lipase activity (DGGMR) is 752.05, the above equation can be expressed as follows.

$$Cs=(Ws\times10^6)/(Vf\times752.05).$$

In such a case, the amount Ws (represented in gram) of the substrate fir measuring lipase activity (DGGMR) mixed at the time of the first mixing can be expressed as follows.

$$Ws=(Cs\times Vf\times MWs)/10^6.$$

That is, $Ws=(Cs\times Vf\times752.05)/10^6.$ (b) Case where a Portion of the Mixture of the Substrate for Measuring Lipase Activity and the Present Modified Silicone Oil is Mixed with Water or an Aqueous Solution The amount of the substrate for measuring lipase activity mixed at the time of the first mixing is set to Ws (represented in gram). The final volume (e.g., the volume adjusted to the designated level) after water or an aqueous solution is mixed at the time of the second mixing is set to Vf (represented in mL). The molecular weight of the substrate for measuring lipase activity is set to MWs. A % (by weight or by volume) of the mixture at the time of the first mixing is mixed with water or an aqueous solution at the time of the second mixing. In this case, the concentration Cs (represented in mM) of the substrate for measuring lipase activity after the second mixing can be expressed by the following equation.

$$Cs=(Ws\times10^6)\times(A/100)/(Vf\times MWs)=(Ws\times A\times10^4)/(Vf\times MWs).$$

Since the molecular weight MWs of the substrate for measuring lipase activity (DGGMR) is 752.05, the above equation can be expressed as follows.

$$Cs=(Ws\times A\times10^4)/(Vf\times752.05).$$

In such a case, the amount Ws (represented in grams) of the substrate for measuring lipase activity mixed at the time of the first mixing can be expressed as follows.

$$Ws=(Cs\times Vf\times MWs)/(A\times10^4).$$

That is, $Ws=(Cs\times Vf\times752.05)/(A\times10^4).$ (3) Amount of the Present Modified Silicone Oil Mixed In the step of mixing DGGMR as a substrate for measuring lipase activity with the present modified silicone oil to prepare a mixture, the amount of the present modified silicone oil to be mixed is not particularly limited.

The concentration of the present modified silicone oil is preferably 0.01% (w/v) or higher after the second mixing for the purpose of producing the emulsion solution composed of stable and uniform micelle particles.

After the second mixing, the concentration of the present modified silicone oil is more preferably 0.05% (w/v) or higher and still more preferably 0.1% (w/v) or higher in view of the above purpose.

After the second mixing, the concentration of the present modified silicone oil is preferably 20% (w/v) or lower in view of the above purpose.

After the second mixing, the concentration of the present modified silicone oil is more preferably 10% (w/v) or lower and still more preferably 5% (w/v) or lower in view of the above purpose.

The preferable concentration of the present modified silicone oil after the second mixing is as described above.

The amount of the DGGMR and that of the present modified silicone oil mixed with each other at the time of first mixing may adequately be determined, so as to adjust the concentration of the present modified silicone oil to the level described above after the second mixing. This is preferable in light of the production procedure.

Regarding the amount of the present modified silicone oil and the concentration thereof, for example, the following cases (a) and (b) may be considered.

(a) Case where all of the Mixture of the Substrate for Measuring Lipase Activity and the Present Modified Silicone Oil is Mixed with Water or an Aqueous Solution The amount of the present modified silicone oil mixed at the time of the first mixing is set to Wp (represented in gram). The final volume (e.g., the volume adjusted to the designated level) after water or an aqueous solution is mixed at the time of the second mixing is set to Vf (represented in mL). The concentration Cp (represented in % (w/v)) of the present modified silicone oil after the second mixing can be expressed by the following equation.

$$Cp=(Wp\times100)/Vf.$$

In this case, the amount Wp (represented in grams) of the present modified silicone oil mixed at the time of the first mixing can be expressed as follows.

$$Wp=(Cp\times Vf)/100.$$

(b) Case where a Portion of the Mixture of the Substrate for Measuring Lipase Activity and the Present Modified Silicone Oil is Mixed with Water or an Aqueous Solution The amount of the present modified silicone oil mixed at the time of the first mixing is set to Wp (represented in grams). The final volume (e.g., the volume adjusted to the designated level) after water or an aqueous solution is mixed at the time of the second mixing is set to Vf (represented in mL). A % (by weight or by volume) of the mixture at the time of the first mixing is mixed with water or an aqueous solution at the time of the second mixing. In this case, the concentration Cp (represented in % (w/v)) of the present modified silicone oil after the second mixing can be expressed by the following equation.

$$Cp=(Wp\times100)\times(A/100)/Vf=(Wp\times A)/Vf.$$

In such a case, the amount Wp (represented in grams) of the present modified silicone oil mixed at the time of the first mixing can be expressed as follows.

$$Wp=(Cp\times Vf)/A.$$

(4) Mixing Procedure

In the step of mixing DGGMR with the present modified silicone oil to prepare a mixture, the DGGMR may be mixed with the present modified silicone oil by any method without particular limitation, provided that DGGMR is mixed with the present modified silicone oil.

According to the present invention, it is not necessary to carry out the mixing in the following manner: DGGMR is mixed into a solution containing an organic solvent (e.g., an alcohol) and the present modified silicone oil; a liquid containing DGGMR is added dropwise and mixed into a solution containing the present modified silicone oil; a liquid containing DGGMR is jet-injected into a solution containing the present modified silicone oil; a solution containing DGGMR and the present modified silicone oil is stirred using a strong mixer at a high speed; a solution containing DGGMR and the present modified silicone oil is subjected to ultrasonication; or the like. Accordingly, the mixing does not necessitate cumbersome or special processing such that skill is required, or it does not necessitate a special apparatus or other items. A common mixer may be used for the mixing at a typical speed. Likewise, a usual procedure may be used for the mixing. In this way, the mixture of the DGGMR and the present modified silicone oil can be prepared.

(5) Temperature at the Time of Mixing

In the step of mixing DGGMR with the present modified silicone oil to prepare a mixture, the temperature at which DGGMR is mixed with the present modified silicone oil is not particularly limited. However, it is preferable that this step be carried out at a temperature near or lower than the cloud point of the present modified silicone oil used for the purpose of producing an emulsion solution composed of stable and uniform micelle particles.

At a cloud point, micelles of a nonionic surfactant, etc., cannot be formed when the temperature of an aqueous solution containing a nonionic surfactant is increased. The cloud point is a temperature at which the aqueous solution becomes clouded. Different surfactants have different cloud points.

In the present invention, the temperature at or near the cloud point of the present modified silicone oil means a temperature within a range plus or minus 25° C. from the cloud point of the present modified silicone oil.

The temperature at or near the cloud point of the present modified silicone oil is preferably a temperature within a range plus or minus 15° C. from the cloud point of the present modified silicone oil, more preferably a temperature within a range plus or minus 10° C. from the cloud point of the present modified silicone oil, and still more preferably a temperature within a range plus or minus 5° C. from the cloud point of the present modified silicone oil.

In the present invention, a step of mixing DGGMR with the present modified silicone oil to prepare a mixture is also preferably carried out at a temperature near or lower than the cloud point of the present modified silicone oil or lower.

For example, KF-351A, which is the present modified silicone oil, has a cloud point of 52° C. (a self-measured value), KF-355A has a cloud point of 67° C. (a self-measured value), and KF-6011 has a cloud point of 64° C. (a self-measured value).

Since KF-354L did not reach a cloud point even at 77° C., which is the upper limit of the preset temperature of a thermostat water bath used for measuring the cloud point, the cloud point exceeds 77° C.

In view of the above purpose, the step of mixing DGGMR with the present modified silicone oil to prepare a mixture is preferably carried out at a temperature within a range plus or minus 25° C. from the cloud point of the present modified silicone oil used or lower, more preferably at a temperature within a range plus or minus 15° C. from the cloud point of the modified silicon point used or lower, still more preferably at a temperature within a range plus or minus 10° C. from the cloud point of the present polymer used or lower, and still more preferably at a temperature within a range plus or minus 5° C. from the cloud point of the present polymer used or lower.

In the step of mixing DGGMR with the present modified silicone oil to prepare a mixture according to the present invention, DGGMR is preferably mixed with the present modified silicone oil at a temperature equal to or higher than the melting point of each of DGGMR and the present modified silicone oil, for the purpose of producing an emulsion solution composed of stable and uniform micelle particles.

In view of the above purpose, the step of mixing DGGMR with the present modified silicone oil to prepare a mixture is carried out more preferably at 2° C. or higher, further preferably at 5° C. or higher, and still more preferably at 10° C. or higher.

(6) Mixing Duration

In the step of mixing DGGMR with the present modified silicone oil to prepare a mixture, the duration of mixing DGGMR with the present modified silicone oil is not particularly limited, provided that the DGGMR can be uniformly mixed with the present modified silicone oil.

Usually, mixing is preferably carried out for 5 minutes or longer for the purpose of producing an emulsion solution composed of stable and uniform micelle particles. In general, a duration of 5 minutes is sufficient.

The duration required for mixing DGGMR with the present modified silicone oil does not have a particular upper limit. For example, the mixing may be carried out for several hours. In light of the idea that time is cost, the duration may usually be within 10 minutes even if the mixing is performed with care.

3. Step of Mixing the Mixture of DGGMR with the Present Modified Silicone Oil with Water or an Aqueous Solution Hereafter, "the step of mixing all or a portion of the mixture prepared in step (b) described in 1 above (i.e., the step of mixing DGGMR with the present modified silicone oil to prepare a mixture) with water or an aqueous solution" is described in detail.

(1) Water or Aqueous Solution

In step (b) described in 1 above; that is, the step of mixing all or a portion of the mixture prepared in step (a) in 1 above with water or an aqueous solution, the water or aqueous solution is not particularly limited.

Examples of the water include, but are not particularly limited to, pure water, distilled water, and purified water.

In addition, this aqueous solution is not particularly limited as long as water is used as a solvent. Examples include aqueous solutions containing at least one substance selected from the group consisting of a lipase promoter, a lipase activator, a colipase, and a buffer.

(a) Lipase Promoter

In the present invention, the lipase promoter that can be contained in the above aqueous solution may be a substance that can promote lipase activity. Examples include, but are not particularly limited to, bile acid and a salt thereof.

The bile acid or salt thereof as the lipase promoter is as described in the "(1) Lipase promoter" section in II. 3 above.

After the second mixing, the concentration of the lipase promoter is preferably 0.2% (w/v) or higher.

After the second mixing, the concentration of the lipase promoter is more preferably 0.4% (w/v) or higher and still more preferably 1% (w/v) or higher.

After the second mixing, the concentration of the lipase promoter is preferably 20% (w/v) or lower.

After the second mixing, the concentration of the lipase promoter is more preferably 10% (w/v) or lower and still more preferably 5% (w/v) or lower.

The preferable concentration of the lipase promoter after the second mixing is as described above.

By taking the ratio of mixing the "mixture of DGGMR and the present modified silicone oil" with the aqueous solution into consideration, the lipase promoter may preferably be introduced into the aqueous solution at adequate concentration, so as to adjust the concentration of the lipase promoter after the second mixing to the level described above.

(b) Lipase Activator

In the present invention, a lipase activator that can be contained in the aqueous solution is not particularly limited, provided that it can activate a lipase. Examples thereof include an ion or salt of an alkaline-earth metal.

The ion or salt of an alkaline-earth metal as the lipase activator is as described in II. 4 "(1) Lipase activator" above.

After the second mixing, the concentration of the lipase activator is preferably 0.1 mM or higher.

After the second mixing, the concentration of the lipase activator is more preferably 1 mM or higher and still more preferably 5 mM or higher.

After the second mixing, the concentration of the lipase activator is preferably 100 mM or lower.

After the second mixing, the concentration of the lipase activator is more preferably 50 mM or lower and still more preferably 25 mM or lower.

The preferable concentration of the lipase activator after the second mixing is as described above.

By taking the ratio of mixing the "mixture of DGGMR and the present modified silicone oil" with the aqueous solution into consideration, the lipase activator may preferably be introduced into the aqueous solution at adequate concentration, so as to adjust the concentration of the lipase activator after the second mixing to the level described above.

(c) Colipase

In the present invention, a colipase that can be contained in an aqueous solution is not particularly limited, provided that it has the effect, function, or activity of a colipase.

The colipase is as described in II. 5 "(1) Colipase" above.

After the second mixing, the activity value of the colipase is preferably 15K Unit/L, or higher.

After the second mixing, the activity value of the colipase is more preferably 150K Unit/L or higher and still more preferably 750K Unit/L or higher.

After the second mixing, the activity value of the colipase is preferably 7,500K Unit/L or lower.

After the second mixing, the activity value of the colipase is more preferably 3,750K Unit/L or lower and still more preferably 2,250K Unit/L or lower.

The preferable activity value of the colipase after the second mixing is as described above.

By taking the ratio of mixing the "mixture of DGGMR and the present modified silicone oil" with the aqueous solution into consideration, the colipase may preferably be introduced into the aqueous solution at adequate activity value, so as to adjust the activity value of the colipase after the second mixing to the level described above.

(d) pH

In the present invention, DGGMR used as the substrate for measuring lipase activity is stable at or near pH 4.

After the second mixing, accordingly, the pH thereof is preferably within a certain range relative to pH 4.

In view of stability of DGGMR, specifically, the pH after the second mixing is preferably from 2 to 7, more preferably from 3 to 5, and still more preferably from 3.5 to 4.5 (the pH values are measured at 20° C.).

The pH level after the second mixing is as described above.

In order to adjust the pH level after the second mixing to the level described above, the pH of the aqueous solution is preferably adjusted to an adequate level.

(e) Buffer

In the present invention, the aqueous solution may contain, as needed, a buffer with buffering capability within the above pH range, so as to keep the pH level after the second mixing within the pH range described in (d) above.

The buffer is as described in II. 8 "(1) Buffer" above.

The concentration of the buffer in this buffer-containing aqueous solution (i.e., a buffer solution) is not particularly limited, as long as the buffering capability can be exerted within a prescribed pH range.

For example, after the second mixing, the concentration of the buffer is preferably 5 mM or higher, more preferably 10 mM or higher, and still more preferably 30 mM or higher.

In addition, after the second mixing, the concentration of the buffer is preferably 500 mM or lower, more preferably 100 mM or lower, and still more preferably 50 mM or lower.

The preferable concentration of the buffer after the second mixing is as described above.

It is preferable that the aqueous solution contain the buffer at an adequate concentration, so as to adjust the concentration of the buffer after the second mixing to the level described above.

(2) Mixing the Mixture of DGGMR and the Present Modified Silicone Oil with Water or Aqueous Solution In the step of mixing all or a portion of the mixture prepared in step (b) described in 1 above (i.e., the step of mixing DGGMR with the present modified silicone oil to prepare a mixture) with water or an aqueous solution, all or a portion of the "mixture of DGGMR with the present modified silicone oil" is mixed with the "water or aqueous solution."

The step of mixing all or a portion of the mixture prepared by mixing DGGMR as a substrate for measuring lipase activity with the present modified silicone oil with water or an aqueous solution is not particularly limited. For example, all or a portion of "the mixture prepared by mixing DGGMR with the present modified silicone oil" may be added to and mixed with "water or an aqueous solution." Alternatively, water or an aqueous solution may be added to and mixed with all or a portion of the mixture prepared by mixing DGGMR with the present modified silicone oil. The step of mixing may be carried out via other means.

The ratio of mixing "the mixture of DGGMR with the present modified silicone oil" with "water or an aqueous solution" is not particularly limited, and the ratio may adequately be determined.

Mixing of "the mixture of DGGMR with the present modified silicone oil" with "the water or aqueous solution" may be considered in view of the following aspects (i) and (ii).

(i) In View of Concentration of DGGMR

As described in detail in the above section 2. "(2) Amount of DGGMR mixed," after the second mixing, the concentration of DGGMR is preferably 0.05 mM or higher, more preferably 0.1 mM or higher, and still more preferably 0.2 mM or higher, in view of the above purpose.

As described in detail in the above section 2. "(2) Amount of DGGMR mixed," also, after the second mixing, the concentration of DGGMR is preferably 2 mM or lower, more preferably 1 mM or lower, and still more preferably 0.8 mM or lower, in view of the above purpose.

Regarding the relationship between the preferable concentration of DGGMR and the final volume after water or an aqueous solution is mixed at the time of the second mixing, for example, the following cases (a) and (b) may be considered.

(a) Case where all of the Mixture of the Substrate for Measuring Lipase Activity and the Present Modified Silicone Oil is Mixed with Water or an Aqueous Solution The amount of the substrate for measuring lipase activity mixed at the time of the first mixing is set to Ws (represented in gram). The final volume (e.g., the volume adjusted to the designated level) after water or an aqueous solution is mixed at the time of the second mixing is set to Vf (represented in mL). The molecular weight of the substrate for measuring lipase activity is set to MWs. In such a case, the concentration Cs (represented in mM) of the substrate for measuring lipase activity after the second mixing can be expressed by the following equation.

$$Cs=(Ws\times10^6)/(Vf\times MWs)$$

Since the molecular weight MWs of the substrate for measuring lipase activity (DGGMR) is 752.05, the above equation can be expressed as follows.

$$Cs=(Ws\times10^6)/(Vf\times752.05)$$

In this case, accordingly, the final volume Vf (represented in mL) after water or an aqueous solution is mixed at the time of the second mixing can be expressed as follows.

$$Vf=(Ws\times10^6)/(Cs\times MWs)$$

That is, $Vf=(Ws\times10^6)/(Cs\times752.05)$.

At the time of the second mixing, accordingly, water or an aqueous solution may be mixed so as to achieve the volume Vf (represented in mL) calculated using the above equation. Thus, a substrate solution for measuring lipase activity comprising the substrate for measuring lipase activity (DGGMR) at a desired concentration can be obtained.

(b) Case where a Portion of the Mixture of the Substrate for Measuring Lipase Activity and the Present Modified Silicone Oil is Mixed with Water or an Aqueous Solution The amount of the substrate for measuring lipase activity mixed at the time of the first mixing is set to Ws (represented in gram). The final volume (e.g., the volume adjusted to the designated level) after water or an aqueous solution is mixed at the time of the second mixing is set to Vf (represented in mL). The molecular weight of the substrate for measuring lipase activity is set to MWs. A % (by weight or by volume) of the mixture at the time of the first mixing is mixed with water or an aqueous solution at the time of the second mixing. In this case, the concentration Cs (represented in mM) of the substrate for measuring lipase activity after the second mixing can be expressed by the following equation.

$$Cs=(Ws\times10^6)\times(A/100)/(Vf\times MWs)=(Ws\times A\times10^4)/(Vf\times MWs)$$

Since the molecular weight MWs of the substrate for measuring lipase activity (DGGMR) is 752.05, the above equation can be expressed as follows.

$$Cs=(Ws\times A\times10^4)/(Vf\times752.05)$$

In this case, accordingly, the final volume Vf (represented in mL) after water or an aqueous solution is mixed at the time of the second mixing can be expressed as follows.

$$Vf=(Ws\times A\times10^4)/(Cs\times MWs)$$

That is, $Vf=(Ws\times A\times10^4)/(Cs\times752.05)$.

At the time of the second mixing, accordingly, water or an aqueous solution may be mixed so as to achieve the volume Vf (represented in mL) calculated using the above equation. Thus, a substrate solution for measuring lipase activity comprising the substrate for measuring lipase activity (DGGMR) at a desired concentration can be obtained.

(ii) In View of Concentration of the Present Modified Silicone Oil

As described in detail in the above section 2. "(3) Amount of the present modified silicone oil mixed," the concentration of the present modified silicone oil after the second mixing is preferably 0.01% (w/v) or higher, more preferably 0.05% (w/v) or higher, and still more preferably 0.1% (w/v) or higher, in view of the above purpose.

As described in detail in the above section 2. "(3) Amount of the present modified silicone oil mixed," also, after the second mixing, the concentration of the present modified silicone oil is preferably 20% (w/v) or lower, more preferably 10% (w/v) or lower, and still more preferably 5% (w/v) or lower, in view of the above purpose.

Regarding the relationship between the preferable concentration of the present modified silicone oil and the final volume after water or an aqueous solution is mixed at the time of the second mixing, for example, the following cases (a) and (b) may be considered.

(a) Case where all of the Mixture of the Substrate for Measuring Lipase Activity and the Present Modified Silicone Oil is Mixed with Water or an Aqueous Solution The amount of the present modified silicone oil mixed at the time of the first mixing is set to Wp (represented in gram). The final volume (e.g., the volume adjusted to the designated level) after water or an aqueous solution is mixed at the time of the second mixing is set to Vf (represented in mL). The concentration Cp (represented in % (w/v)) of the present modified silicone oil after the second mixing can be expressed by the following equation.

$$Cp=(Wp\times100)/Vf$$

In this case, accordingly, the final volume Vf (represented in mL) after water or an aqueous solution is mixed at the time of the second mixing can be expressed as follows.

$$Vf=(Wp\times100)/Cp$$

At the time of the second mixing, accordingly, water or an aqueous solution may be mixed so as to achieve the volume Vf (represented in mL) calculated using the above equation. Thus, a substrate solution for measuring lipase activity containing the present modified silicone oil at a desired concentration can be obtained.

(b) Case where a Portion of the Mixture of the Substrate for Measuring Lipase Activity and the Present Modified Silicone Oil is Mixed with Water or an Aqueous Solution The amount of the present modified silicone oil mixed at the time of the first mixing is set to Wp (represented in gram). The final volume (e.g., the volume adjusted to the designated level) after water or an aqueous solution is mixed at the time of the second mixing is set to Vf (represented in mL). A % (by weight or by volume) of the mixture at the time of the first mixing is mixed with water or an aqueous solution at the time of the second mixing. In this case, the concentration Cp (represented in % (w/v)) of the present modified silicone oil after the second mixing can be expressed by the following equation.

$$Cp=(Wp\times100)\times(A/100)/Vf=(Wp\times A)/Vf$$

In this case, accordingly, the final volume Vf (represented in mL) after water or an aqueous solution is mixed at the time of the second mixing can be expressed as follows.

$$Vf=(Wp\times A)/Cp$$

At the time of the second mixing, accordingly, water or an aqueous solution may be mixed so as to achieve the volume Vf (represented in mL) calculated using the above equation. Thus, a substrate solution for measuring lipase activity containing the present modified silicone oil at a desired concentration can be obtained.

The step of mixing all or a portion of the mixture prepared by mixing DGGMR as a substrate for measuring lipase activity and the present modified silicone oil with water or an aqueous solution may be carried out through two or more stages (steps).

This step is preferably carried out through a plurality of stages (steps) for the purpose of producing an emulsion solution composed of stable and uniform micelle particles.

The procedure in which this step is carried out through a plurality of stages is not particularly limited. For example, procedures carried out through the following stages <A> and <B> may be employed.

Stage <A> in which a certain quantity of water or an aqueous solution is mixed with all or a portion of the mixture prepared by mixing DGGMR and the present modified silicone oil.

Stage <B> in which an additional certain quantity of water or an aqueous solution is mixed with the mixed liquid after the above water or aqueous solution is mixed with the mixture obtained at the stage <A> (i.e., the mixture of DGGMR with the present modified silicone oil).

In this case, the volume (fixed volume) of the "water or aqueous solution" mixed with "all or a portion of the mixture prepared by mixing DGGMR with the present modified silicone oil" at the stage <A> is set to Va (represented in mL). The final volume after "an additional certain quantity of water or an aqueous solution" is mixed with the mixed liquid at the stage <B> (i.e., the final volume after water or an aqueous solution is mixed at the time of the second mixing) (e.g., the volume adjusted to the designated level) is set to Vf (represented in mL). For the purpose of producing an emulsion solution composed of stable and uniform micelle particles, the ratio (Vf/Va) calculated by dividing Vf by Va is preferably from 1 to 500.

Specifically, the Va and Vf values (volumes) are preferably selected, so as to adjust the ratio (Vf/Va) calculated by dividing Vf by Va within a range from 1 to 500, in view of the above purpose.

In view of the above purpose, also, the ratio (Vf/Va) calculated by dividing Vf by Va is more preferably within a range from 2 to 200 and still more preferably within a range from 5 to 100.

In view of the above purpose, specifically, the Va and Vf values (volumes) are selected, so that the ratio (Vf/Va) calculated by dividing Vf by Va is more preferably adjusted within a range from 2 to 200 and still more preferably within a range from 5 to 100.

Stage <A> in which a certain quantity of water or an aqueous solution is mixed with all or a portion of the mixture prepared by mixing DGGMR and the present modified silicone oil is not particularly limited. For example, all or a portion of "the mixture prepared by mixing DGGMR with the present modified silicone oil" may be added to and mixed with a certain quantity of "water or an aqueous solution." Alternatively, a certain quantity of "water or an aqueous solution" may be added to and mixed with all or a portion of "the mixture prepared by mixing DGGMR with the present modified silicone oil." Stage <A> may be carried out via other means.

Stage <B> in which an additional certain quantity of water or an aqueous solution is mixed with the mixed liquid after water or an aqueous solution is mixed with the mixture obtained at the stage <A> (i.e., the mixture of DGGMR with the present modified silicone oil) is not particularly limited. For example, "a mixture obtained by mixing the mixture obtained at the stage <A> (i.e., the mixture of DGGMR with the present modified silicone oil) and water or an aqueous solution" may be added to and mixed with a certain quantity of "water or an aqueous solution." Alternatively, a certain quantity of "water or an aqueous solution" may be added to and mixed with "a mixture obtained by mixing the mixture obtained at the stage <A> (i.e., the mixture of DGGMR with the present modified silicone oil) and water or an aqueous solution." Stage <B> may be carried out via other means.

(3) Mixing Procedure

In the step of mixing all or a portion of the mixture prepared by mixing DGGMR as a substrate for measuring lipase activity and the present modified silicone oil with water or an aqueous solution, a method for mixing all or a portion of the mixture with water or an aqueous solution is not particularly limited, provided that the mixture can be mixed with the water or aqueous solution.

It is not necessary to carry out the mixing in the following manner: the substrate for measuring lipase activity is mixed into a solution containing an organic solvent (e.g., an alcohol); a liquid containing the substrate for measuring lipase activity is added dropwise and mixed into a solution; a liquid containing the substrate for measuring lipase activity is jet-injected into a solution; a substrate solution for measuring lipase activity is stirred using a strong mixer at a high speed; a substrate solution for measuring lipase activity is subjected to ultrasonication; or the like. Accordingly, the mixing does not necessitate cumbersome or special processing such that skill is required, or it does not necessitate a special apparatus or other items. A common mixer may be used for the mixing at a typical speed. Likewise, a usual procedure may be used for the mixing. In this way, all or a portion of the mixture of DGGMR as a substrate for measuring lipase activity and the present modified silicone oil can be mixed with water or an aqueous solution.

(4) Temperature at the Time of Mixing

In the step of mixing all or a portion of the mixture prepared by mixing DGGMR as a substrate for measuring lipase activity and the present modified silicone oil with water or an aqueous solution, the temperature at which all or a portion of the mixture is mixed with water or an aqueous solution is not particularly limited. However, it is preferable that this step be carried out at a temperature equal to or lower than the cloud point of the present modified silicone oil used, for the purpose of producing an emulsion solution composed of stable and uniform micelle particles.

The step of mixing all or a portion of the mixture prepared by mixing DGGMR and the present modified silicone oil with water or an aqueous solution is more preferably carried out at a temperature that is 10° C. lower than the cloud point of the present modified silicone oil or lower, and it is still more preferably carried out at 25° C. or lower, in view of the above purpose.

The step of mixing all or a portion of the mixture prepared by mixing DGGMR and the present modified silicone oil with water or an aqueous solution is preferably carried out at a temperature equal to or higher than the melting point of each of DGGMR and the present modified silicone oil, for the purpose of producing an emulsion solution composed of stable and uniform micelle particles.

The step of mixing all or a portion of the mixture prepared by mixing DGGMR and the present modified silicone oil with water or an aqueous solution is more preferably carried out at 10° C. or higher and still more preferably at 15° C. or higher, in view of the above purpose.

(5) Mixing Duration

In the step of mixing all or a portion of the mixture prepared by mixing DGGMR as a substrate for measuring lipase activity and the present modified silicone oil with water or an aqueous solution, the duration of mixing all or a portion of the mixture with water or an aqueous solution is not particularly limited, provided that the mixture of DGGMR with the present modified silicone oil can be uniformly mixed with the water or an aqueous solution.

Usually, mixing is preferably carried out for 5 minutes or longer for the purpose of producing an emulsified solution of a substrate for measuring lipase activity composed of stable and uniform micelle particles. In general, a duration of 5 minutes is sufficient.

The duration required for mixing the mixture of DGGMR with the present modified silicone oil with water or an aqueous solution does not have a particular upper limit. For example, the mixing may be carried out for several hours. In light of the idea that time is cost, the duration may usually be within 10 minutes even if the mixing is performed with care.

[2] The Reagent for Measuring Lipase Activity of the Present Invention

I. Overview

The reagent for measuring lipase activity of the present invention comprises a substrate solution for measuring lipase activity comprising an emulsion solution comprising micelle particles of 1,2-o-dilauryl-rac-glycero-3-glutaric acid (6'-methylresorufin) ester (DGGMR) and side-chain-type nonreactive polyether-modified-type modified silicone oil (the emulsion solution and the substrate solution for measuring lipase activity are as described in detail in the section "[1] Substrate solution for measuring lipase activity of the present invention").

The reagent for measuring lipase activity of the present invention is excellent in terms of storage stability because of the constitution described above.

II. Reagent for Measuring Lipase Activity

1. Constitution of a Reagent for Measuring Lipase Activity Etc.

The reagent for measuring lipase activity of the present invention may consist of the substrate solution for measuring lipase activity of the present invention, or it may comprise the substrate solution for measuring lipase activity of the present invention and other reagent members (e.g., a reagent kit).

For the reasons (a) and (b) described below, the reagent for measuring lipase activity of the present invention is preferably in the form of a reagent kit comprising the substrate solution for measuring lipase activity of the present invention and other reagent members.

(a) The substrate for measuring lipase activity DGGMR) according to the present invention is stable at or near pH 4. In contrast, the activity of the lipase is optimal at or near pH 8. That is, suitable pH ranges are different.

(b) When an all-in-one reagent contains the substrate for measuring lipase activity (DGGMR) according to the present invention, a colipase, and, as a lipase promoter, bile acid or a salt thereof, the substrate for measuring lipase activity (DGGMR) becomes unstable.

Thus, the reagent kit preferably comprises the substrate solution for measuring lipase activity according to the present invention and other reagent members. In this case, one reagent containing the substrate for measuring lipase activity (DGGMR) according to the present invention preferably has a pH at or near 4. At least one of the other reagent members to be combined with the above one reagent preferably has a pH of 8 or higher. In addition, it is preferable that the substrate for measuring lipase activity (DGGMR) according to the present invention, a colipase, and, as a lipase promoter, bile acid or a salt thereof be not included in one reagent.

Preferably, the reagent for measuring lipase activity according to the present invention is a two-component reagent kit consisting of the substrate solution for measuring lipase activity according to the present invention and another reagent member.

In this case, it is more preferable that another reagent member be used as the first reagent, and the substrate solution for measuring lipase activity according to the present invention be used as the second reagent.

In this case, it is still more preferable that another reagent member has a pH of 8 or higher and the substrate solution for measuring lipase activity according to the present invention has a pH at or near 4.

It is further preferable that the substrate solution for measuring lipase activity according to the present invention does not simultaneously comprise both "the colipase" and "the bile acid or salt thereof as a lipase promoter," and that the another reagent member comprises at least one of "the colipase" and "the bile acid or salt thereof as a lipase promoter."

The reagent for measuring lipase activity according to the present invention may be used to carry out measurement by an end-point method. Alternatively, the reagent may be used to carry out measurement by a reaction rate method (a rate method). While an adequate method may be selected according to need, measurement is preferably carried out by the reaction rate method (the rate method).

Regarding the reagent for measuring lipase activity of the present invention, the substrate for measuring lipase activity (DGGMR) of the present invention is brought into contact with the sample to allow the reaction to proceed, and 1,2-o-dilauryl-rac-glycerol and glutaric acid (6'-methylresorufin) ester are generated as a result of hydrolysis catalyzed by the lipase. However, the glutaric acid (6'-methylresorufin) ester is unstable and is thus hydrolyzed readily and naturally to give 6'-methylresorufin ($\lambda$max: 580 nm).

Accordingly, an increase in the resulting 6'-methylresorufin is measured by reading the absorbance at or near 580 nm, and the activity value of the lipase contained in the sample may then be determined. In such a case, a single-wavelength method or a two-wavelength method may be employed.

When the reagent for measuring lipase activity of the present invention is subjected to measurement, the temperature may be set to, for example, 30° C. or 37° C., so that the measurement reaction can proceed and a reaction component, such as an enzyme involved in the measurement reaction, are not inactivated, denatured, or modified due to heat.

The measurement reaction involving the use of the reagent for measuring lipase activity of the present invention may be initiated by, for example, adding the substrate for measuring lipase activity (DGGMR) of the present invention or adding the sample.

The measurement reaction involving the use of the reagent for measuring lipase activity of the present invention may be performed manually or using a device (e.g., an automated analyzer).

Also, all or a part of the reagent members of the reagent for measuring lipase activity of the present invention may be liquid.

The substrate solution for measuring lipase activity of the present invention, by itself, may be marketed and used for measuring lipase activity in a sample.

The substrate solution for measuring lipase activity of the present invention may be marketed in combination with another reagent member or other reagents and used for measuring lipase activity in a sample.

Examples of another reagent member and other reagents include: a buffer, a sample diluent; a reagent diluent; a reagent containing a substance used for calibration; and a reagent containing a substance used for quality control.

2. Specific Examples of the Reagent for Measuring Lipase Activity of the Present Invention Specific examples of the reagent for measuring lipase activity of the present invention are described below.

(1) Example 1

(a) First reagent (an aqueous solution (pH 8.3 at 20° C.) containing the following reagent components at the respective concentrations described below).

Sodium deoxycholate (a lipase promoter) 2% (w/v)
Calcium chloride (a lipase activator) 5 mM
Colipase (derived from a porcine pancreas; Roche Diagnostics K. K. (Japan)) 375K Unit/L (5 mg/L)
Bicine (a buffer) 40 mM (b) Second reagent (a substrate solution for measuring lipase activity according to the present invention) (an aqueous solution (pH 4.0 at 20° C.) containing the following reagent components at the respective concentrations described below)

1,2-o-dilauryl-rac-glycero-3-glutaric acid (6'-methylresorufin) ester (DGGMR) (Roche Diagnostics K. K. (Japan)) (a substrate for measuring lipase activity) 0.3 mM
Side-chain-type nonreactive polyether-modified-type modified silicone oil 0.3% (w/v)
L-Tartaric acid (a buffer) 40 mM (2) Example 2

(a) First Reagent (the Aqueous Solution (pH 8.4 at 20° C.) Containing the Following Reagent Components at the Respective Concentrations Described Below)

Sodium taurodeoxycholate (a lipase promoter) 2% (w/v)
Sodium deoxycholate (a lipase promoter) 0.2% (w/v)
Calcium chloride (a lipase activator) 5 mM
Colipase (derived from a porcine pancreas; Roche Diagnostics K. K. (Japan)) 150K Unit/L (2 mg/L)
Tris(hydroxymethyl)aminomethane (Tris) (a buffer) 40 mM (b) Second Reagent (the Substrate Solution for Measuring Lipase Activity According to the Present Invention) (an Aqueous Solution Containing the Following Reagent Components at the Respective Concentrations Described Below)

1,2-o-dilauryl-rac-glycero-3-glutaric acid (6'-methylresorufin) ester (DGGMR) (Roche Diagnostics K. K. (Japan)) (a substrate for measuring lipase activity) 0.6 mM
Side-chain-type nonreactive polyether-modified-type modified silicone oil 0.3% (w/v)
Sodium taurodeoxycholate (a lipase promoter) 2% (w/v)

[3] The Method for Measuring Lipase Activity in a Sample of the Present Invention I. Overview The method for measuring lipase activity in a sample of the present invention involves the use of a substrate solution for measuring lipase activity comprising an emulsion solution comprising micelle particles of 1,2-o-dilauryl-rac-glycero-3-glutaric acid (6'-methylresorufin) ester (DGGMR) and side-chain-type nonreactive polyether-modified-type modified silicone oil, thereby measuring lipase activity in a sample (the emulsion solution and the substrate solution for measuring lipase activity are described in detail in the section "[1] Substrate solution for measuring lipase activity of the present invention." The reagent for measuring lipase activity is also described in detail in the [2] Reagent for measuring lipase activity of the present invention, as described above).

The method for measuring lipase activity in a sample of the present invention can provide accurately measured values over a long period of time because of the constitution as described above.

II. Method for Measuring Lipase Activity

1. Method for Measuring Lipase Activity in a Sample

When lipase activity in a sample is measured by the method for measuring lipase activity in a sample of the present invention of the present invention, such measurement may be carried out by an end-point method. Alternatively, measurement may be carried out by a reaction rate method (a rate method). While an adequate method may be selected according to need, measurement is preferably carried out by the reaction rate method (the rate method).

When the lipase activity in a sample is to be measured by the method for measuring lipase activity in a sample of the present invention, a one-step method in which measurement is carried out through one step or a multi-step method in which measurement is carried out through two or more steps may be appropriately selected to carry out the measurement.

When the reagent for measuring lipase activity used for measuring lipase activity in a sample is composed of the first reagent, the second reagent, and other reagent(s) (one or more reagents); that is, when such reagent is composed of three or more reagents, the measurement reaction may be performed through the number of steps required for the measurement using these reagents (two or more steps or three or more steps, according to need), to measure the lipase activity in the sample.

In the method for measuring lipase activity in a sample of the present invention, the substrate for measuring lipase activity (DGGMR) of the present invention is brought into contact and allowed to react with the sample, and 1,2-o-dilauryl-rac-glycerol and glutaric acid (6'-methylresorufin) ester are generated as a result of hydrolysis catalyzed by a lipase. This glutaric acid (6'-methylresorufin) ester is unstable and is thus hydrolyzed readily and naturally to give 6'-methylresorufin ($\lambda$max: 580 nm).

Accordingly, an increase in the resulting 6'-methylresorufin may be measured by reading the absorbance at or near 580 nm, and the activity value of the lipase contained in the sample may be determined. In such a case, a single-wavelength method or a two-wavelength method may be employed.

The activity value of the lipase contained in the sample may be calculated based on the absorbance (or transmittance) measured or a change in the absorbance (or transmittance) by an appropriately selected method. For example, the activity value may be calculated based on the absorbance (or transmittance) measured on the basis of the molar absorption coefficient of 6'-methylresorufin, or the activity value may be calculated in comparison with the absorbance (or transmittance) of a reference material (e.g., a standard solution or reference serum) with the known lipase activity value.

The activity value of the lipase contained in the sample is preferably calculated by subtracting a reagent blank value from the absorbance (or transmittance) obtained by measuring the sample.

In the method for measuring lipase activity in a sample of the present invention, the temperature during the measurement may be set at, for example, 30° C. or 37° C. that is within a temperature range, such that the measurement reaction can proceed and reaction components such as an enzyme involved in the measurement reaction are not inactivated, denatured, or modified by to heat.

In the method for measuring lipase activity in a sample of the present invention, the measurement reaction may be initiated with the addition of, for example, the substrate for measuring lipase activity of the present invention or with the addition of the sample.

In the method for measuring lipase activity in a sample of the present invention, the measurement may be performed manually or using a device (e.g., an automated analyzer).

2. Specific Examples of the Method for Measuring Lipase Activity in a Sample

Hereafter, specific examples of the method for measuring lipase activity in a sample of the present invention are provided.

(1) Reagent for Measuring Lipase Activity (a) First Reagent

The first reagent described in the above section [2] II. 2 (1) (a) was used as the first reagent in this specific example regarding the measurement.

(b) Second Reagent

The second reagent described in the above section [2] II. 2 (1) (b) was used as the second reagent in this specific example regarding the measurement.

(2) Sample

Human serum was used as a sample.

(3) Measurement (a) First Step

The sample of (2) and the first reagent of (1) (a) are mixed to prepare a mixed liquid.

The amount of each of the sample and the first reagent to be mixed may be adequately determined depending on the amount of the second reagent, the activity value of the lipase contained in the sample, and other conditions.

For example, the amount of the sample is preferably within a range from 0.5 to 100 µL. and the amount of the first reagent is preferably within a range from 20 to 1,000 µL, in general.

After a mixed liquid is prepared, the resulting mixed liquid is then subjected to incubation.

The incubation period is not particularly limited. In general, it is preferably within 20 minutes, more preferably within 10 minutes, and still more preferably within 5 minutes.

Incubation may be carried out at a temperature above the temperature at which the above mixed liquid is frozen.

At the time of measurement, in general, a reaction rate is increased as a temperature is raised. Accordingly, a higher temperature is preferable.

If the temperature is too high, however, the components (e.g., an enzyme) involved in the measurement reaction are denatured or inactivated. Accordingly, it is necessary that incubation be performed at a temperature lower than the temperature at which the components (e.g., an enzyme) involved with the measurement reaction are denatured or inactivated.

In general, incubation is preferably carried out at from 2° C. to 70° C., more preferably from 20° C. to 37° C., and still more preferably from 30° C. to 37° C.

If the components (e.g., an enzyme) involved with the measurement reaction are heat-resistant components (e.g., a thermostable enzyme), the temperature may be much higher.

By preparing a mixed liquid of the sample and the first reagent and subjecting the mixed liquid to incubation, the lipase contained in the sample is brought into contact with the reagent components of the first reagent, and the lipase is then promoted and activated by such components.

(b) Second Step

The "mixed liquid of the sample and the first reagent" prepared in the first step is mixed with the second reagent of (1) (b) above. The resultant is designated as the final reaction solution.

The amount of the second reagent to be mixed may be adequately determined depending on the amount of the sample, the amount of the first reagent, the activity value of the lipase contained in the sample, settings of an analyzer used, and other conditions.

For example, the amount of the second reagent is preferably within a range from 10 to 1,000 µL, in general.

After the final reaction solution is prepared, the resulting mixed liquid is then subjected to incubation.

The incubation period is not particularly limited. In general, it is preferably within 20 minutes, more preferably within 10 minutes, and still more preferably within 5 minutes.

Incubation may be carried out at a temperature above the temperature at which the above final reaction solution is frozen.

At the time of measurement, in general, a reaction rate is increased as a temperature is raised. Accordingly, a higher temperature is preferable.

If the temperature is too high, however, the components (e.g., an enzyme) involved with the measurement reaction are denatured or inactivated. Accordingly, it is necessary that incubation be performed at a temperature lower than the temperature at which the components (e.g., an enzyme) involved with the measurement reaction are denatured or inactivated.

In general, incubation is carried out at preferably from 2° C. to 70° C., more preferably from 20° C. to 37° C., and still more preferably from 30° C. to 37° C.

If the components (e.g., enzymes) involved with the measurement reaction are heat-resistant components (e.g., thermostable enzymes), the temperature may be much higher.

As a result of preparation and incubation of the final reaction solution, the lipase activity is promoted and activated in the first step, the measurement reaction is initiated in the second step, and the reaction for the measurement of the activity of the lipase contained in the sample is then proceeded.

According to the present invention, specifically, the second reagent (the substrate solution for measuring lipase activity of the present invention), which is an emulsified substrate solution composed of stable and uniform micelle particles, is brought into contact with the lipase contained in the sample in the second stage. As a result of hydrolysis catalyzed by the lipase, 1,2-o-dilauryl-rac-glycerol and glutaric acid (6'-methylresorufin) ester are generated from the substrate for measuring lipase activity (DGGMR) of the present invention.

This glutaric acid (6'-methylresorufin) ester is unstable and is thus hydrolyzed readily and naturally to give 6'-methylresorufin (λmax: 580 nm).

The maximum absorption wavelength (λmax) of the resulting 6'-methylresorufin is 580 nm. The absorbance (or transmittance) of the final reaction solution derived from this 6'-methylresorufin is measured by reading the absorbance (or transmittance) at or near 580 nm.

Subsequently, the activity value of the lipase contained in the sample is calculated based on the absorbance (or transmittance) measured or a change in the absorbance (or transmittance).

The activity value may be calculated based on the absorbance (or transmittance) measured on the basis of the molar absorption coefficient of 6'-methylresorufin, or the activity value may be calculated in comparison with the absorbance (or transmittance) of a reference material (e.g., a standard solution or reference serum) with the known lipase activity value.

The activity value of the lipase contained in the sample is preferably calculated based on the difference in the absorbance (ΔAbs.) determined by subtracting a reagent blank value from the absorbance (or transmittance) of the final reaction solution obtained by measuring the sample.

[4] The Emulsion Solution of the Present Invention

The emulsion solution of the present invention comprises micelle particles of 1,2-o-dilauryl-rac-glycero-3-glutaric acid (6'-methylresorufin) ester (DGGMR) and side-chain-type nonreactive polyether-modified-type modified silicone oil. (The emulsion solution and the substrate solution for measuring lipase activity are as described in detail in the section "[1] Substrate solution for measuring lipase activity of the present invention." The reagent for measuring lipase activity is as described in detail in the section "[2] Reagent for measuring lipase activity of the present invention." The method for measuring lipase activity in a sample is as described in detail in the section "[3] Method for measuring lipase activity in a sample of the present invention.")

The emulsion solution of the present invention is excellent in terms of storage stability because of the constitution described above.

[5] Method for Stabilizing the Substrate Solution for Measuring Lipase Activity of the Present Invention The method fir stabilizing the substrate solution for measuring lipase activity involving the use of 1,2-o-dilauryl-rac-glycero-3-glutaric acid (6'-methylresorufin) ester (DGGMR) as the substrate for measuring lipase activity according to the present invention is characterized in that the substrate solution comprises the side-chain-type nonreactive polyether-modified-type modified silicone oil together with 1,2-o-dilauryl-rac-glycero-3-glutaric acid (6'-methylresorufin) ester. (The emulsion solution and the substrate solution for measuring lipase activity are as described in detail in the section "[1] Substrate solution for measuring lipase activity of the present invention." The reagent for measuring lipase activity is as described in detail in the section "[2] Reagent for measuring lipase activity of the present invention." The method for measuring lipase activity in a sample is as described in detail in the section "[3] Method for measuring lipase activity in a sample of the present invention.")

The method for stabilizing the substrate solution for measuring lipase activity of the present invention is capable of improving storage stability of the substrate solution for measuring lipase activity because of the constitution described above.

[6] Method for Stabilizing the Emulsion Solution of the Present Invention

The method for stabilizing the emulsion solution comprising micelle particles of 1,2-o-dilauryl-rac-glycero-3-glutaric acid (6'-methylresorufin) ester (DGGMR) according to the present invention is characterized in that the emulsion solution comprises the side-chain-type nonreactive polyether-modified-type modified silicone oil together with 1,2-o-dilauryl-rac-glycero-3-glutaric acid (6'-methylresorufin) ester. (The emulsion solution and the substrate solution for measuring lipase activity are as described in detail in the section "[1] Substrate solution for measuring lipase activity of the present invention." The reagent for measuring lipase activity is as described in detail in the section "[2] Reagent for measuring lipase activity of the present invention." The method for measuring lipase activity in a sample is as described in detail in the section "[3] Method for measuring lipase activity in a sample of the present invention.")

The method for stabilizing the emulsion solution of the present invention is capable of improving storage stability of the emulsion solution because of the constitution described above.

EXAMPLES

Hereafter, the present invention is described in greater detail with reference to the examples, although the present invention is not limited to these examples.

[Example 1] (Verification of the Effects of the Substrate Solution for Measuring Lipase Activity of the Present Invention-1)

The effects of the substrate solution for measuring lipase activity of the present invention concerning storage stability were inspected.

1. Preparation of Reagent

The substrate solution for measuring lipase activity of the present invention (i.e., the substrate solution for measuring lipase activity comprising the emulsion solution of the present invention) was prepared.

Separately, a control substrate solution for measuring lipase activity was prepared.

In addition, a buffer solution was prepared.

[1] Preparation of the Substrate Solution for Measuring Lipase Activity of the Present Invention (1) A portion (0.09 g) of the substrate for measuring lipase activity of the present invention; i.e., 1,2-o-dilauryl-rac-glycero-3-glutaric acid (6'-methylresorufin) ester (DGGMR) (the distributor: Roche Diagnostics K. K. (Japan)), was fractionated into a beaker (volume: 10 mL).

(2) Subsequently, a portion (4.0 g) of the side-chain-type nonreactive modified silicone oil (polyether modified type); KF-351A (the distributor: Shin-Etsu Chemical Co., Ltd. (Japan)), was fractionated and added to the beaker of (1).

(3) After the addition (2) above, the content of the beaker was stirred at room temperature (25° C.) to mix the substrate for measuring lipase activity (DGGMR) and the present modified silicone oil (KF-351A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of 2% (w/v) sodium taurodeoxycholate aqueous solution" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, (all) the "mixture prepared by mixing the substrate for measuring lipase activity (DGGMR) and the present modified silicone oil" was mixed with the "certain quantity (4.0 mL) of 2% (w/v) sodium taurodeoxycholate aqueous solution."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(5) Subsequently, a certain quantity of 2% (w/v) sodium taurodeoxycholate aqueous solution was further added to the "mixed liquid prepared by mixing the mixture (i.e., the mixture of the substrate for measuring lipase activity (DG-GMR) and the present modified silicone oil) and a certain quantity of 2% (w/v) sodium taurodeoxycholate aqueous solution" obtained in (4) above, to bring the final volume of the solution to 200 ml.

(6) Through the procedure described above, the substrate solution for measuring lipase activity of the present invention (the substrate for measuring lipase activity: DGGMR; the present modified silicone oil: KF-351A) was prepared.

In the substrate solution for measuring lipase activity, the concentration of the substrate for measuring lipase activity (DGGMR) was 0.6 mM, and that of the present modified silicone oil (KF-351A) was 2.0% (w/v).

In addition, neither concentration gradient nor strong turbidity was observed in the substrate solution for measuring lipase activity. It was visually confirmed that the substrate solution was uniformly mixed.

[2] Preparation of a Control Substrate Solution for Measuring Lipase Activity (1) A portion (0.09 g) of the substrate for measuring lipase activity; i.e., 1,2-o-dilauryl-rac-glycero-3-glutaric acid (6'-methylresorufin) ester (DGGMR) (the distributor: Roche Diagnostics K. K. (Japan)), was fractionated into a beaker (volume: 10 mL).

(2) Subsequently, a portion (1.0 g) of a nonionic surfactant (NIKKOL BT-7; polyoxyethylene (7) secondary alkyl ether; the distributor: Nikko Chemicals Co., Ltd. (Japan)), was fractionated and added to the beaker of (1).

(3) After the addition (2) above, the content of the beaker was stirred at room temperature (25° C.) to mix the substrate for measuring lipase activity (DGGMR) and the surfactant in the beaker.

This process of mixing (stirring) was performed for 5 minutes to prepare a "mixture of the substrate for measuring lipase activity (DGGMR) and the surfactant."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of 2% (w/v) sodium taurodeoxycholate aqueous solution" was added to (all) the "mixture of the substrate for measuring lipase activity (DGGMR) and the surfactant" in the beaker of (3) with stirring at room temperature (25° C.) with the use of a micropipette.

After the addition, stirring was continued at room temperature (25° C.) for 5 minutes. In this way, (all) the "mixture prepared by mixing the substrate for measuring lipase activity (DGGMR) and the surfactant" was mixed with the "certain quantity (4.0 mL) of 2% (w/v) sodium taurodeoxycholate aqueous solution."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(5) Subsequently, a certain quantity of 2% (w/v) sodium taurodeoxycholate aqueous solution was further added to the "mixed liquid prepared by mixing the mixture (i.e., the mixture of the substrate for measuring lipase activity (DG-GMR) and the surfactant) and a certain quantity of 2% (w/v) sodium taurodeoxycholate aqueous solution" obtained in (4) above, to bring the final volume of the solution to 200 ml.

(6) Through the procedure described above, a control substrate solution for measuring lipase activity (i.e., a substrate solution for measuring lipase activity (the substrate for measuring lipase activity: DGGMR; surfactant: NIKKOL BT-7)) was prepared.

In the control substrate solution for measuring lipase activity, the concentration of the substrate for measuring lipase activity (DGGMR) is 0.6 mM, and that of the surfactant is 0.5% (w/v).

In addition, neither concentration gradient nor strong turbidity was observed in the substrate solution for measuring lipase activity. It was visually confirmed that the substrate solution was uniformly mixed.

[3] Preparation of Buffer Solution

The reagent component below was dissolved at designated concentration in pure water, and the pH level was adjusted to 8.4 (20° C.) to prepare the buffer solution.

Bicine (a buffer) 40 mM

2. Storage of Reagent (1) The substrate solution for measuring lipase activity of the present invention prepared in 1 [1] above was stored at 25° C. in the dark for 30 days.

(2) The control substrate solution for measuring lipase activity prepared in 1 [2] above was stored at 25° ° C. in the dark for 30 days.

3. Measurement of the Amount of Substrate Degradation (1) The buffer solution of the day on which it was produced in 1 [3] above was designated as the first reagent, and the substrate solution for measuring lipase activity of the present invention stored at 25° C. (in the dark) for 30 days as described in 2 (1) above was designated as the second reagent.

The second reagent (960 µL) was added to 1,600 µl of the first reagent to prepare a mixed liquid.

(2) The Absorption Curve of the Mixed Liquid Obtained in (1) Above was Measured.

The absorption curve was measured with the use of the DU-7500 series spectrophotometer (the distributor: Beckman Coulter, Inc. (Japan)).

(3) The procedures described in (1) and (2) above were performed in the same manner, except that the substrate solution for measuring lipase activity of the present invention as the second reagent in (1) above was replaced with the control substrate solution for measuring lipase activity stored at 25° C.; (in the dark) for 30 days in 2 (2) above. The absorption curve of the mixed liquid when the control substrate solution for measuring lipase activity of 2 (2) above was used as the second reagent was measured.

4. Results of Measurement

FIG. 1 shows the absorption curve of the mixed liquid when the substrate solution for measuring lipase activity of the present invention of 2 (1) above was used as the second reagent measured in 3 above.

Figure 2:
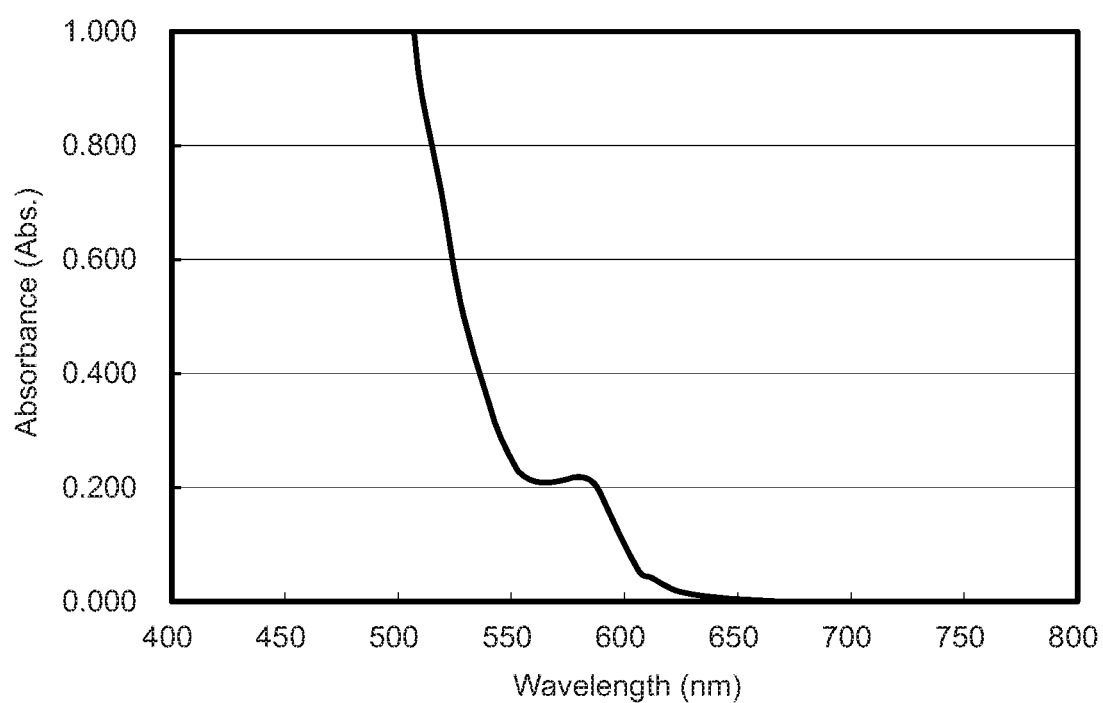
FIG. 2 shows an absorption curve of a mixture using the stored substrate solution for measuring lipase activity as a control sample.

FIG. 2 shows the absorption curve of the mixed liquid when the control substrate solution for measuring lipase activity of 2 (2) above was used as the second reagent measured in 3 above.

In FIGS. 1 and 2, the horizontal axis indicates the wavelength (represented in run), and the vertical axis indicates the absorbance (represented in Abs).

5. Discussion (1) During the storage of an emulsion solution comprising micelle particles of DGGMR and a substrate solution for measuring lipase activity involving the use of DGGMR as a substrate for measuring lipase activity, DGGMR is gradually hydrolyzed.

As a result of DGGMR degradation, 6'-methylresorufin is generated in the end.

The 6'-methylresorufin has a maximum absorption wavelength at 580 nm.

On the basis of the peak height (the extent of the increase) at 580 nm indicating the generation of 6'-methylresorufin in the absorption curves shown in FIGS. 1 and 2, respectively, the amount of 6'-methylresorufin generated; i.e., the amount of DGGMR degraded (the amount of hydrolysis), was determined.

(2) As a result, the amount of DGGMR degraded as a result of the storage of the substrate solution for measuring lipase activity of the present invention (FIG. 1) at 25° C. (in the dark) for 30 days was 4.8%.

In contrast, the amount of DGGMR degraded as a result of the storage of the control substrate solution for measuring lipase activity (FIG. 2) at 25° C. (in the dark) for 30 days was 8.9%.

(3) More specifically, the amount of DGGMR degraded as a result of the storage of the substrate solution for measuring lipase activity of the present invention is as small as 54% of the amount of DGGMR degraded as a result of the storage of the control substrate solution for measuring lipase activity.

(4) Thus, the present invention was found to be capable of effectively suppressing DGGMR degradation, excellent in storage stability, and capable of accurate measurement over a long period of time.

[Example 2] (Verification of the Effects of the Substrate Solution for Measuring Lipase Activity of the Present Invention-2)

The effects of the substrate solution for measuring lipase activity of the present invention concerning storage stability were reexamined.

1. Reagent

A substrate solution for measuring lipase activity of the present invention (i.e., a substrate solution for measuring lipase activity comprising the emulsion solution of the present invention) was prepared.

As a control, a substrate solution of a commercially available reagent was used.

A buffer solution was also prepared.

[1] Preparation of the Substrate Solution for Measuring Lipase Activity of the Present Invention (1) A portion (0.045 g) of the substrate for measuring lipase activity of the present invention; i.e., 1,2-o-dilauryl-rac-glycero-3-glutaric acid (6'-methylresorufin) ester (DG-GMR) (the distributor: Roche Diagnostics K. K. (Japan)), was fractionated into a beaker (volume: 10 mL).

(2) Subsequently, a portion (0.6 g) of the side-chain-type nonreactive modified silicone oil (polyether modified type): KF-355A (the distributor: Shin-Etsu Chemical Co., Ltd. (Japan)), was fractionated and added to the beaker of (1).

(3) After the addition (2) above, the content of the beaker was stirred at 67° C. to mix the substrate for measuring lipase activity (DGGMR) and the present modified silicone oil (KF-355A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor. AS ONE Corporation (Japan)) and rotating a magnet bar in the beaker while setting the dial of a control unit of the multi-stirrer at "3."

(4) Subsequently, a "certain quantity (4.0 mL) of 40 mM L-sodium tartrate buffer (pH 4.0 at 20° C.)" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of 40 mM L-sodium tartrate buffer (pH 4.0 at 20° C.)" was mixed with (all) the "mixture prepared by mixing the substrate for measuring lipase activity (DG-GMR) and the present modified silicone oil."

Stirring was carried out by mounting the beaker on a multi-stirrer (the model: M-3; the distributor AS ONE Corporation (Japan)) and rotating a magnet bar in the beaker while setting the dial of a control unit of the multi-stirrer at "3."

(5) Subsequently, a certain quantity of 40 mM l-sodium tartrate buffer (pH 4.0 at 20° C.) was further added to the "mixed liquid prepared by mixing the mixture (i.e., the mixture of the substrate for measuring lipase activity (DG-GMR) and the present modified silicone oil) and a certain quantity of 40 mM L-sodium tartrate buffer (pH 4.0 at 20° C.)" of (4) above, so as to bring the final volume to 200 ml.

(6) Through the procedure described above, the substrate solution for measuring lipase activity of the present invention (the substrate for measuring lipase activity: DGGMR; the present modified silicone oil: KF-355A) was prepared.

In the substrate solution for measuring lipase activity, the concentration of the substrate for measuring lipase activity (DGGMR) was 0.3 mM, and that of the present modified silicone oil (KF-355A) thereof was 0.3% (w/v).

In addition, neither concentration gradient nor strong turbidity was observed in the substrate solution for measuring lipase activity. It was visually confirmed that the substrate solution was uniformly mixed.

[2] Commercially Available Control Reagent

A commercially available reagent for measuring lipase activity (a reagent kit for measuring lipase activity); that is, Liquitech Lipase Color II (the distributor: Roche Diagnostics K. K. (Japan)), was used as a control reagent.

The "Liquitech Lipase Color II" (hereafter, it is occasionally referred to as a "commercially available control reagent") comprises a first reagent (i.e., a buffer solution) and a second reagent (i.e., a substrate solution) (it comprises DGGMR as a substrate for measuring lipase activity at 0.27 mM).

A "substrate solution" of the "commercially available control reagent" was used in this example.

[3] Preparation of Buffer Solution

The reagent component below was dissolved at designated concentration in pure water, and the pH level was adjusted to 8.4 (20° C.) to prepare a buffer solution.

Bicine (a buffer) 40 mM

2. Storage of Reagent (1) The substrate solution for measuring lipase activity of the present invention prepared in 1 [1] above was stored at 30° C. in the dark for 35 days.

(2) The substrate solution of the commercially available control reagent prepared in 1 [2] above was stored at 30° C. in the dark for 35 days.

3. Measurement of the Amount of Substrate Degradation (1) The buffer solution of the day on which it was produced in 1 [3] above designated as the first reagent and the substrate solution for measuring lipase activity of the present invention stored at 30° C. (in the dark) in 2 (1) above designated as the second reagent were subjected to the measurement described below.

The measurement was carried out on the day of initiation of storage of the substrate solution for measuring lipase activity of the present invention (Day 0), 7 days after the initiation of storage, 15 days after the initiation of storage, 21 days after the initiation of storage, and 35 days after the initiation of storage with the use of the substrate solution for measuring lipase activity of the present invention stored for the designated period of time.

At the outset, 960 μL of the second reagent was added to 1,600 μl of the first reagent to prepare a mixed liquid.

(2) Subsequently, the absorbance of the mixed liquid obtained in (1) above was measured at 580 nm with the use of the DU-7500 series spectrophotometer (the distributor: Beckman Coulter, Inc. (Japan)).

(3) Subsequently, the absorbance of the buffer solution of the day on which it was produced in 1 [3] above was measured at 580 nm as a blank test with the use of the DU-7500 series spectrophotometer (the distributor: Beckman Coulter, Inc. (Japan)).

(4) Subsequently, the difference in the absorbance was determined by subtracting the absorbance measured in (3) above (i.e., a blank value) from the absorbance measured in (2) above.

(5) Subsequently, the difference in the absorbance determined in (4) above was divided by the molar absorption coefficient of 6'-methylresorufin at 580 nm (i.e., 60.65 (represented in cm×μmol$^{-1}$)), so as to calculate the concentration of 6'-methylresorufin generated upon DGGMR degradation during storage (represented in mM).

(6) Subsequently, the concentration of 6'-methylresorufin (represented in mM) generated upon degradation during storage determined in (5) above was divided by the concentration of DGGMR (0.3 mM) of the substrate solution for measuring lipase activity of the present invention of 1 [1] above, so as to calculate the ratio of the concentration of 6'-methylresorufin generated relative to the concentration of DGGMR (1 mM) (represented in %).

Specifically, the ratio of DGGMR degraded during storage of the reagent relative to the concentration of DGGMR (1 n vi) in the reagent (i.e., the ratio of DGGMR degradation) was calculated (represented in %).

(7) The procedures described in (1) to (6) above were performed in the same manner, except that the substrate solution for measuring lipase activity of the present invention as the second reagent in (1) above was replaced with the substrate solution of the commercially available control reagent stored at 30° C. (in the dark) for 35 days in 2 (2) above, and the concentration (0.3 mM) of DGGMR in the substrate solution for measuring lipase activity of the present invention in (6) was replaced with the concentration (0.27 mM) of DGGMR in the substrate solution of the commercially available control reagent of 1 [2] above, so as to calculate the ratio of the concentration of 6'-methylresorufin generated relative to the concentration of DGGMR (1 mM) when the substrate solution of the commercially available control reagent of 2 (2) above was used as the second reagent (represented in %).

Specifically, the ratio of DGGMR degraded during storage of the reagent relative to the concentration of DGGMR (1 mM) in the reagent (the ratio of DGGMR degradation) was calculated (represented in %).

4. Results of Measurement

Figure 3:
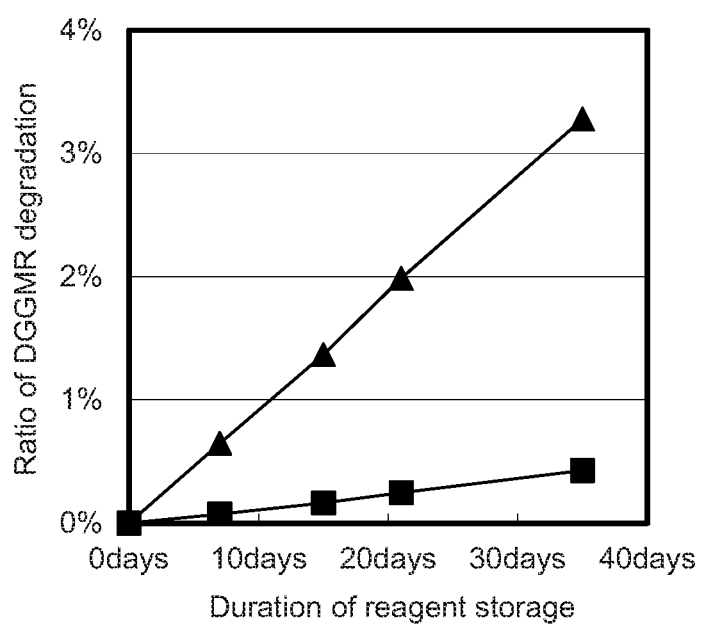
FIG. 3 shows the percentage of DGGMR degraded at the time of storage of the substrate solution for measuring lipase activity of the present invention and a substrate solution of a commercially available control reagent.

Table 1 and FIG. 3 show "the ratio of DGGMR degraded during storage of the reagent relative to the concentration of DGGMR (1 mM) in the reagent" (i.e., the ratio of DGGMR degradation) (represented in %) when the substrate solution for measuring lipase activity of the present invention of 2 (1) above was used as the second reagent, which was determined in 3 above.

Table 1 and FIG. 3 also show "the ratio of DGGMR degraded during storage of the reagent relative to the concentration of DGGMR (1 mM) in the reagent" (i.e., the ratio of DGGMR degradation) (represented in %) when the substrate solution of the commercially available control reagent of 2 (2) above was used as the second reagent, which was determined in 3 above.

Table 1 and FIG. 3 each show "the ratio of DGGMR degradation" determined over time relative to "the ratio of DGGMR degradation" designated as "0" on the day of initiation of storage (Day 0).

In FIG. 3, the horizontal axis indicates the duration of reagent storage (represented in the number of days), and the vertical axis indicates the ratio of DGGMR degradation (represented in %).

In FIG. 3, "the ratio of DGGMR degradation" of the substrate solution for measuring lipase activity of the present invention is represented by the symbol "■" and "the ratio of DGGMR degradation" of the substrate solution of the commercially available control reagent is represented by the symbol "▲."

TABLE 1

| Duration of reagent storage | Ratio of DGGMR degradation | |
| --- | --- | --- |
| | Substrate solution for measuring lipase activity of the invention | Substrate solution of commercially available control reagent |
| 0 days | 0.0% | 0.0% |
| 7 days | 0.1% | 0.6% |
| 15 days | 0.2% | 1.4% |
| 21 days | 0.2% | 2.0% |
| 35 days | 0.4% | 3.3% |

5. Discussion (1) Table 1 and FIG. 3 demonstrate that, as a result of storage at 30° C. for 15 days. "the ratio of DGGMR degradation" of the substrate solution fir measuring lipase activity of the present invention is 0.2% and "the ratio of DGGMR degradation" of the substrate solution of the commercially available control reagent is 1.4%.

Specifically. "the ratio of DGGMR degradation" of the substrate solution for measuring lipase activity of the present invention is as low as 14%, of "the ratio of DGGMR degradation" of the substrate solution of the commercially available control reagent.

(2) Table 1 and FIG. 3 demonstrate that, as a result of storage at 30° C. for 35 days, "the ratio of DGGMR degradation" of the substrate solution for measuring lipase activity of the present invention is 0.4%, and "the ratio of DGGMR degradation" of the substrate solution of the commercially available control reagent is 3.3%.

Specifically, "the ratio of DGGMR degradation" of the substrate solution for measuring lipase activity of the present invention is as low as 12% of "the ratio of DGGMR degradation" of the substrate solution of the commercially available control reagent.

(3) On the basis of the results attained in this example, accordingly, the present invention was found to be capable of effectively suppressing DGGMR degradation, excellent in storage stability, and capable of accurate measurement over a long period of time.

[Example 3] (Verification of the Effects of the Substrate Solution for Measuring Lipase Activity of the Present Invention-3)

The effects of the substrate solution for measuring lipase activity of the present invention concerning storage stability were reexamined.

1. Reagent

In total, four types of the substrate solutions for measuring lipase activity of the present invention (the substrate solutions for measuring lipase activity comprising the emulsion solution of the present invention) were prepared.

As a control, a substrate solution of a commercially available reagent was used.

A buffer solution was also prepared.

[1] Preparation of the Substrate Solution for Measuring Lipase Activity of the Present Invention (1) A portion (0.09 g) of the substrate for measuring lipase activity of the present invention; i.e., 1,2-o-dilauryl-rac-glycero-3-glutaric acid (6'-methylresorufin) ester (DGGMR) (the distributor Roche Diagnostics K. K. (Japan)), was fractionated into each of 4 beakers (volume: 10 mL).

(2) Subsequently, a portion (4.0 g) of each of the four types of side-chain-type nonreactive modified silicone oil (polyether modified type) (a) to (d) below was fractionated and separately added to each of the beakers of (1).

(a) KF-351A (the distributor: Shin-Etsu Chemical Co., Ltd. (Japan))

(b) KF-354A (the distributor: Shin-Etsu Chemical Co., Ltd. (Japan))

(c) KF-355A (the distributor: Shin-Etsu Chemical Co., Ltd. (Japan))

(d) KF-6011 (the distributor: Shin-Etsu Chemical Co., Ltd. (Japan))

(3) After the addition (2) above, the content of each beaker was stirred at 67° C. to mix the substrate for measuring lipase activity (DGGMR) and the present modified silicone oil in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of pure water" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of pure water" was mixed with (all) the "mixture prepared by mixing the substrate for measuring lipase activity (DGGMR) and the present modified silicone oil."

Stirring was carried out by mounting the beaker on a multi-stirrer (the model: M-3; the distributor AS ONE Corporation (Japan)) and rotating a magnet bar in the beaker while setting the dial of a control unit of the multi-stirrer at "3."

(5) Subsequently, a certain quantity of pure water was further added to the "mixed liquid prepared by mixing the mixture (i.e., the mixture of the substrate for measuring lipase activity (DGGMR) and the present modified silicone oil) and a certain quantity of pure water" of (4) above, so as to bring the final volume to 200 ml.

(6) Through the procedure described above, a total of four types of the substrate solutions for measuring lipase activity of the present invention (A) to (I)) below were prepared.

In these substrate solutions for measuring lipase activity (four types in total), the concentration of the substrate for measuring lipase activity (DGGMR) was 0.6 mM, and that of the present modified silicone oil was 2.0% (w/v).

In addition, neither concentration gradient nor strong turbidity was observed in these substrate solutions for measuring lipase activity (four types in total). It was visually confirmed that the substrate solutions were uniformly mixed.

(A) A substrate solution for measuring lipase activity-A (the substrate for measuring lipase activity: DGGMR; the present modified silicone oil: KF-351A)

(B) A substrate solution for measuring lipase activity-B (the substrate for measuring lipase activity: DGGMR; the present modified silicone oil: KF-354A)

(C) A substrate solution for measuring lipase activity-C (the substrate for measuring lipase activity: DGGMR; the present modified silicone oil: KF-355A)

(D)) A substrate solution for measuring lipase activity-D (the substrate for measuring lipase activity: DGGMR; the present modified silicone oil: KF-6011)

[2] Commercially Available Control Reagent

A commercially available reagent for measuring lipase activity (a reagent kit for measuring lipase activity); that is, Liquitech Lipase Color II (the distributor: Roche Diagnostics K. K. (Japan)), was used as a control reagent.

The "Liquitech Lipase Color II" (hereafter, it is occasionally referred to as a "commercially available control reagent") comprises a first reagent (i.e., a buffer solution) and a second reagent (i.e., a substrate solution) (it comprises DGGMR as a substrate for measuring lipase activity at 0.27 mM).

A "substrate solution" of the "commercially available control reagent" was used in this example.

[3] Preparation of Buffer Solution

The reagent component below was dissolved at designated concentration in pure water, and the pH level was adjusted to 8.4 (20° C.) to prepare the buffer solution.

Bicine (a buffer) 40 mM

2. Storage of Reagent (1) The four types of substrate solutions for measuring lipase activity of the present invention (A) to (D) described in 1 [11] (6) above were stored at 25° C. in the dark for 31 days.

(2) The substrate solution of the commercially available control reagent of 1 [2] above was stored at 25° C. in the dark for 32 days.

3. Measurement of the Amount of Substrate Degradation (1) The buffer solution of the day on which it was produced in 1 [3] above designated as the first reagent and the "(A) the substrate solution for measuring lipase activity-A" stored at 25° C. (in the dark) in 2 (1) above designated as the second reagent were subjected to the measurement described below.

The measurement was carried out on the day of initiation of storage of the substrate solution for measuring lipase activity of the present invention (Day 0), 5 days after the initiation of storage, 23 days after the initiation of storage, and 31 days after the initiation of storage with the use of "(A) the substrate solution for measuring lipase activity-A" stored for the designated period of time.

At the outset, 960 µL of the second reagent was added to 1,600 µl of the first reagent to prepare a mixed liquid.

(2) Subsequently, the absorbance of the mixed liquid obtained in (1) above was measured at 580 nm with the use of the DU-7500 series spectrophotometer (the distributor: Beckman Coulter, Inc. (Japan)).

(3) Subsequently, the absorbance of the buffer solution of the day on which it was produced in 1 [3] above was measured at 580 nm as a blank test with the use of the DU-7500 series spectrophotometer (the distributor Beckman Coulter, Inc. (Japan)).

(4) Subsequently, the difference in the absorbance was determined by subtracting the absorbance measured in (3) above (i.e., a blank value) from the absorbance measured in (2) above.

(5) Subsequently, the difference in the absorbance determined in (4) above was divided by the molar absorption coefficient of 6'-methylresorufin at 580 nm (i.e., 60.65 (represented in cm×µmol$^{-1}$)), so as to calculate the concentration of 6'-methylresorufin generated upon DGGMR degradation during storage (represented in mM).

(6) Subsequently, the concentration of 6'-methylresorufin (represented in mM) generated upon degradation during storage determined in (5) above was divided by the concentration of DGGMR (0.6 mM) of "(A) the substrate solution for measuring lipase activity-A" of 1 [1] (6) above, so as to calculate the ratio of the concentration of 6'-methylresorufin generated relative to the concentration of DGGMR (1 mM) (represented in %).

Specifically, "the ratio of DGGMR degraded during storage of the reagent relative to the concentration of DGGMR (1 mM) in the reagent" (i.e., the ratio of DGGMR degradation) was calculated (represented in %).

(7) The procedures described in (1) to (6) above were performed in the same manner, except that "(A) the substrate solution for measuring lipase activity-A" as the second reagent in (1) above was replaced with "(B) the substrate solution for measuring lipase activity-B" stored at 25° C. (in the dark) for 31 days in 2 (1) above, so as to calculate the ratio of the concentration of 6'-methylresorufin generated relative to the concentration of DGGMR (1 mM) when "(B) the substrate solution for measuring lipase activity-B" of 2 (1) above was used as the second reagent (represented in %).

Specifically, "the ratio of DGGMR degraded during storage of the reagent relative to the concentration of DGGMR (1 mM) in the reagent" (i.e., the ratio of DGGMR degradation) was calculated (represented in %).

(8) The procedures described in (1) to (6) above were performed in the same manner, except that "(A) the substrate solution for measuring lipase activity-A" as the second reagent in (1) above was replaced with "(C) the substrate solution for measuring lipase activity-C" stored at 25° C. (in the dark) for 31 days in 2 (1) above, so as to calculate the ratio of the concentration of 6'-methylresorufin generated relative to the concentration of DGGMR (1 mM) when "(C) the substrate solution for measuring lipase activity-C" of 2 (1) above was used as the second reagent (represented in %).

Specifically, "the ratio of DGGMR degraded during storage of the reagent relative to the concentration of DGGMR (1 mM) in the reagent" was calculated (represented in %).

(9) The procedures described in (1) to (6) above were performed in the same manner, except that "(A) the substrate solution for measuring lipase activity-A" as the second reagent in (1) above was replaced with "(D) the substrate solution for measuring lipase activity-D" stored at 25° C. (in the dark) for 31 days in 2 (1) above, so as to calculate the ratio of the concentration of 6'-methylresorufin generated relative to the concentration of DGGMR (1 mM) when "(I) the substrate solution for measuring lipase activity-D" of 2 (1) above was used as the second reagent (represented in %).

Specifically, "the ratio of DGGMR degraded during storage of the reagent relative to the concentration of DGGMR (1 mM) in the reagent" (i.e., the ratio of DGGMR degradation) was calculated (represented in %).

(10) Also, the procedures described in (1) to (6) above were performed in the same manner, except that "(A) the substrate solution for measuring lipase activity-A" as the second reagent in (1) above was replaced with the substrate solution of the commercially available control reagent stored at 25° C. (in the dark) for 32 days in 2 (2) above, the measurement in (1) was carried out on the day of initiation of storage (Day 0), 8 days after the initiation of storage, 15 days after the initiation of storage, 21 days after the initiation of storage, 29 days after the initiation of storage, and 32 days after the initiation of storage, and the concentration of DGGMR (0.6 mM) in "(A) the substrate solution for measuring lipase activity-A" in (6) was replaced with the concentration of DGGMR (0.27 mM) in the substrate solution of the commercially available control reagent of 1 [2] above, so as to calculate the ratio of the concentration of 6'-methylresorufin generated relative to the concentration of DGGMR (1 mM) when the substrate solution of the commercially available control reagent of 2 (2) above was used as the second reagent (represented in %).

Specifically. "the ratio of DGGMR degraded during storage of the reagent relative to the concentration of DGGMR (1 mM) in the reagent" (i.e., the ratio of DGGMR degradation) was calculated (represented in %).

4. Results of Measurement

Figure 4:
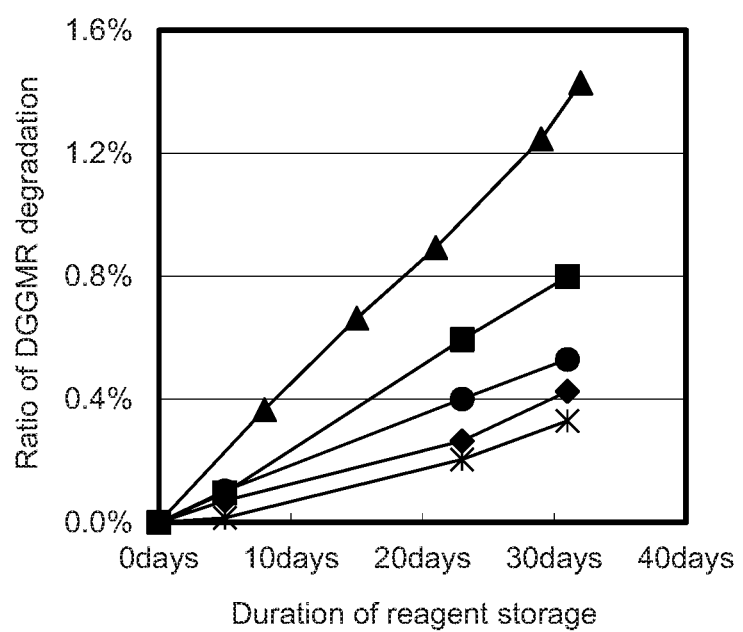
FIG. 4 shows the percentage of DGGMR degraded at the time of storage of the substrate solution for measuring lipase activity of the present invention and a substrate solution of a commercially available control reagent.

Table 2 and FIG. 4 show "the ratio of DGGMR degraded during storage of the reagent relative to the concentration of DGGMR (1 mM) in the reagent" (i.e., the ratio of DGGMR degradation) (represented in %) when the four types of substrate solutions for measuring lipase activity of the present invention (A) to (D) of 2 (1) above were used as the second reagents, which was determined in 3 above.

Table 2 and FIG. 4 also show "the ratio of DGGMR degraded during storage of the reagent relative to the concentration of DGGMR (1 mM) in the reagent" (i.e., the ratio of DGGMR degradation) (represented in %) when the substrate solution of the commercially available control reagent of 2 (2) above was used as the second reagent, which was determined in 3 above.

Table 2 and FIG. 4 each show "the ratio of DGGMR degradation" determined over time relative to "the ratio of DGGMR degradation" designated as "0" on the day of initiation of storage (Day 0).

In FIG. 4, the horizontal axis indicates the duration of reagent storage (represented in the number of days), and the vertical axis indicates the ratio of DGGMR degradation (represented in %).

In FIG. 4. "the ratio of DGGMR degradation" of the substrate solution for measuring lipase activity of the present invention (i.e., "(A) the substrate solution for measuring lipase activity-A") is represented by the symbol "*," "the ratio of DGGMR degradation" of "(B) the substrate solution for measuring lipase activity-B" is represented by the symbol "♦," "the ratio of DGGMR degradation" of "(C) the substrate solution for measuring lipase activity-C" is represented by the symbol "■," "the ratio of DGGMR degradation" of "(D) the substrate solution for measuring lipase activity-D" is represented by the symbol "•," and "the ratio of DGGMR degradation" of the substrate solution of the commercially available control reagent is represented by the symbol "▲."

TABLE 2

| Duration of reagent storage | Ratio of DGGMR degradation | | | |
|---|---|---|---|---|
| | Substrate solution for measuring lipase activity-A | Substrate solution for measuring lipase activity-B | Substrate solution for measuring lipase activity-C | Substrate solution Tor measuring lipase activity-D |
| 0 days | 0.0% | 0.0% | 0.0% | 0.0% |
| 5 days | 0.0% | 0.1% | 0.1% | 0.1% |
| 23 days | 0.2% | 0.3% | 0.6% | 0.4% |
| 31 days | 0.3% | 0.4% | 0.8% | 0.5% |

| Duration of reagent storage | Ratio of DGGMR degradation Substrate solution of commercially available control reagent |
|---|---|
| 0 days | 0.0% |
| 8 days | 0.4% |
| 15 days | 0.7% |
| 21 days | 0.9% |
| 29 days | 1.2% |
| 32 days | 1.4% |

5. Discussion (1) Table 2 and FIG. 4 demonstrate that, as a result of storage at 25° C. for 31 days, "the ratio of DGGMR degradation" of the substrate solution for measuring lipase activity of the present invention (i.e., "(A) the substrate solution for measuring lipase activity-A") is 0.3%, "the ratio of DGGMR degradation" of "(B) the substrate solution for measuring lipase activity-B" is 0.4%, "the ratio of DGGMR degradation" of "(C) the substrate solution for measuring lipase activity-C" is 0.8%, and "the ratio of DGGMR degradation" of "(D) the substrate solution for measuring lipase activity-D" is 0.5%.

Table 2 and FIG. 4 also demonstrate that, as a result of storage at 25° C. for 32 days, "the ratio of DGGMR degradation" of the substrate solution of the commercially available control reagent is 1.4%.

Specifically, "the ratio of DGGMR degradation" of any of the four types of substrate solutions for measuring lipase activity of the present invention (A) to (D) is significantly lower than "the ratio of DGGMR degradation" of the substrate solution of the commercially available control reagent.

(2) On the basis of the results attained in this example, accordingly, the present invention was found to be capable of effectively suppressing DGGMR degradation, excellent in storage stability, and capable of accurate measurement over a long period of time.

[Example 4] (Verification of the Effects of the Substrate Solution for Measuring Lipase Activity of the Present Invention-4)

The effects of the substrate solution for measuring lipase activity of the present invention concerning storage stability were reexamined.

1. Reagent

The substrate solution for measuring lipase activity of the present invention (i.e., the substrate solution for measuring lipase activity comprising the emulsion solution of the present invention) was prepared.

As a control, a substrate solution of a commercially available reagent was used.

A buffer solution was also prepared.

[1] Preparation of the Substrate Solution for Measuring Lipase Activity of the Present Invention (1) A portion (0.045 g) of the substrate for measuring lipase activity of the present invention; i.e., 1,2-o-dilauryl-rac-glycero-3-glutaric acid (6'-methylresorufin) ester (DG-GMR) (the distributor: Roche Diagnostics K. K. (Japan)), was fractionated into a beaker (volume: 10 mL).

(2) Subsequently, a portion (0.6 g) of the side-chain-type nonreactive modified silicone oil (polyether modified type); KF-355A (the distributor: Shin-Etsu Chemical Co., Ltd. (Japan)), was fractionated and added to the beaker of (1).

(3) After the addition (2) above, the content of the beaker was stirred at 67° C. to mix the substrate for measuring lipase activity (DGGMR) and the present modified silicone oil (KF-355A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of 40 mM L-sodium tartrate buffer (pH 4.0 at 20° C.)" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of 40 mM L-sodium tartrate buffer (pH 4.0 at 20° C.)" was mixed with (all) the "mixture prepared by mixing the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(5) Subsequently, a certain quantity of 40 mM L-sodium tartrate buffer (pH 4.0 at 20° C.) was further added to the "mixed liquid prepared by mixing the mixture (i.e., the mixture of the substrate for measuring lipase activity (DGGMR) and the present modified silicone oil) and a certain quantity of 40 mM L-sodium tartrate buffer (pH 4.0 at 20° C.)" of (4) above, so as to bring the final volume to 200 ml.

(6) Through the procedure described above, the substrate solution for measuring lipase activity of the present invention (the substrate for measuring lipase activity: DGGMR; the present modified silicone oil: KF-355A) was prepared.

In the substrate solution for measuring lipase activity, the concentration of the substrate for measuring lipase activity (DGGMR) was 0.3 mM, and that of the present modified silicone oil (KF-355A) was 0.3% (w/v).

In addition, neither concentration gradient nor strong turbidity was observed in the substrate solution for measuring lipase activity. It was visually confirmed that the substrate solution was uniformly mixed.

[2] Commercially Available Control Reagent

A commercially available reagent for measuring lipase activity (a reagent kit for measuring lipase activity); that is, Liquitech Lipase Color II (the distributor: Roche Diagnostics K. K. (Japan)), was used as a control.

The "Liquitech Lipase Color II" (hereafter, it is occasionally referred to as the "commercially available control reagent") is composed of a first reagent (buffer solution) and a second reagent (substrate solution), which comprises, as a substrate for measuring lipase activity. DGGMR at 0.27 mM.

The "substrate solution" of the "commercially available control reagent" was subjected to the discussion in this example.

[3] Preparation of Buffer Solution

The reagent component below was dissolved at designated concentration in pure water, and the pH level was adjusted to 8.4 (20° C.) to prepare the buffer solution.

Bicine (a buffer) 40 mM

2. Storage of Reagent (1) The substrate solution for measuring lipase activity of the present invention prepared in 1 [1] above was stored at 30° C. in the dark for 35 days.

(2) The substrate solution of the commercially available control reagent prepared in 1 [2] above was stored at 30° C. in the dark for 35 days.

3. Measurement of the Amount of Substrate Degradation (1) The buffer solution of the day on which it was produced in 1 [3] above designated as the first reagent and the substrate solution for measuring lipase activity of the present invention stored at 30° C. (in the dark) in 2 (1) above designated as the second reagent were subjected to the measurement described below.

The measurement was carried out on the day of initiation of storage of the substrate solution for measuring lipase activity of the present invention (Day 0), 7 days after the initiation of storage, 15 days after the initiation of storage, 21 days after the initiation of storage, and 35 days after the initiation of storage with the use of the substrate solution for measuring lipase activity of the present invention stored for the designated period of time.

At the outset, 960 µL of the second reagent was added to 1,600 µl of the first reagent to prepare a mixed liquid.

(2) Subsequently, the absorbance of the mixed liquid obtained in (1) above was measured at 580 nm with the use of the DU-7500 series spectrophotometer (the distributor: Beckman Coulter, Inc. (Japan)).

(3) Subsequently, the absorbance of the buffer of the day on which it was produced in 1 [3] above was measured at 580 nm as a blank test with the use of the DU-7500 series spectrophotometer (the distributor: Beckman Coulter, Inc. (Japan)).

(4) Subsequently, the difference in the absorbance was determined by subtracting the absorbance measured in (3) above (i.e., a blank value) from the absorbance measured in (2) above.

(5) Subsequently, the difference in the absorbance determined in (4) above was divided by the molar absorption coefficient of 6'-methylresorufin at 580 nm (i.e., 60.65 (represented in $cm \times \mu mol^{-1}$)), so as to calculate the concentration of 6'-methylresorufin generated upon DGGMR degradation during storage (represented in mM).

(6) Subsequently, the concentration of 6'-methylresorufin (represented in mM) generated upon degradation during storage determined in (5) above was divided by the concentration of DGGMR (0.3 mM) of the substrate solution for measuring lipase activity of the present invention of 1 [1] above, so as to calculate the ratio of the concentration of 6'-methylresorufin generated relative to the concentration of DGGMR (1 mM) (represented in %).

Specifically, "the ratio of DGGMR degraded during storage of the reagent relative to the concentration of DGGMR (1 mM) in the reagent" (i.e., the ratio of DGGMR degradation) was calculated (represented in %).

(7) The procedures described in (1) to (6) above were performed in the same manner, except that the substrate solution for measuring lipase activity of the present invention as the second reagent in (1) above was replaced with the substrate solution of the commercially available control reagent stored at 30° C. (in the dark) for 35 days in 2 (2) above, the measurement in (1) was carried out on the day of initiation of storage (Day 0), 7 days after the initiation of storage, 15 days after the initiation of storage, 21 days after the initiation of storage, and 35 days after the initiation of storage, and the concentration of DGGMR (0.3 mM) in the substrate solution for measuring lipase activity of the present invention of (6) above was replaced with the concentration of DGGMR (0.27 mM) in the substrate solution of the commercially available control reagent of 1 [2] above, so as to calculate the ratio of the concentration of 6'-methylresorufin generated relative to the concentration of DGGMR (1 mM) when the substrate solution of the commercially available control reagent of 2 (2) above was used as the second reagent (represented in %).

Specifically, "the ratio of DGGMR degraded during storage of the reagent relative to the concentration of DGGMR (1 mM) in the reagent" (i.e., the ratio of DGGMR degradation) was calculated (represented in %).

4. Results of Measurement

Figure 5:
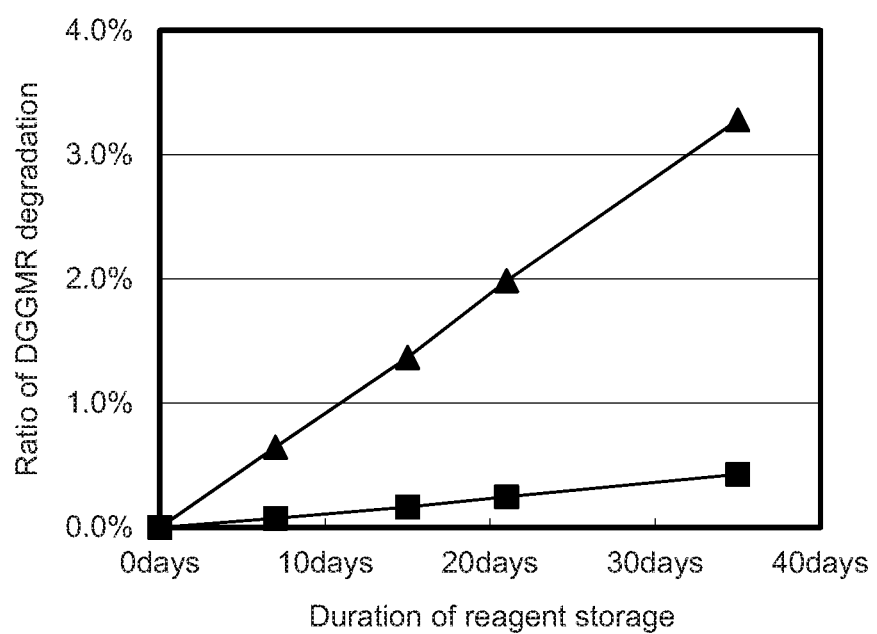
FIG. 5 shows the percentage of DGGMR degraded at the time of storage of the substrate solution for measuring lipase activity of the present invention and a substrate solution of a commercially available control reagent.

Table 3 and FIG. 5 show "the ratio of DGGMR degraded during storage of the reagent relative to the concentration of DGGMR (1 mM) in the reagent" (i.e., the ratio of DGGMR degradation) (represented in %) when the substrate solution for measuring lipase activity of the present invention of 2 (1) above was used as the second reagent, which was determined in 3 above.

Table 3 and FIG. 5 also show "the ratio of DGGMR degraded during storage of the reagent relative to the concentration of DGGMR (1 mM) in the reagent" (i.e., the ratio of DGGMR degradation) (represented in %) when the substrate solution of the commercially available control reagent of 2 (2) above was used as the second reagent, which was determined in 3 above.

Table 3 and FIG. 5 each show "the ratio of DGGMR degradation" determined over time relative to "the ratio of DGGMR degradation" designated as "0" on the day of initiation of storage (Day 0).

In FIG. 5, the horizontal axis indicates the duration of reagent storage (represented in the number of days), and the vertical axis indicates the ratio of DGGMR degradation (represented in %).

In FIG. 5, "the ratio of DGGMR degradation" of the substrate solution for measuring lipase activity of the present invention is represented by the symbol "■" and "the ratio of DGGMR degradation" of the substrate solution of the commercially available control reagent is represented by the symbol "▲."

TABLE 3

| Duration of reagent storage | Ratio of DGGMR degradation | |
| --- | --- | --- |
| | Substrate solution for measuring lipase activity of the invention | Substrate solution of commercially available control reagent |
| 0 days | 0.0% | 0.0% |
| 7 days | 0.1% | 0.6% |
| 15 days | 0.2% | 1.4% |
| 21 days | 0.2% | 2.0% |
| 35 days | 0.4% | 3.3% |

5. Discussion (1) Table 3 and FIG. 5 demonstrate that, as a result of storage at 30° C. for 35 days, "the ratio of DGGMR degradation" of the substrate solution for measuring lipase activity of the present invention is 0.4%

Table 3 and FIG. 5 also demonstrate that, as a result of storage at 30° C. for 35 days, "the ratio of DGGMR degradation" of the substrate solution of the commercially available control reagent is 3.3%.

Specifically, "the ratio of DGGMR degradation" of the substrate solution for measuring lipase activity of the present invention is significantly lower than "the ratio of DGGMR degradation" of the substrate solution of the commercially available control reagent.

(2) On the basis of the results attained in this example, accordingly, the present invention was found to be capable of effectively suppressing DGGMR degradation, excellent in storage stability, and capable of accurate measurement over a long period of time.

[Example 5] (Verification of the Effects of the Substrate Solution for Measuring Lipase Activity of the Present Invention-5)

The effects of the substrate solution for measuring lipase activity of the present invention concerning storage stability were reexamined.

1. Reagent

The substrate solution for measuring lipase activity of the present invention (i.e., the substrate solution for measuring lipase activity comprising the emulsion solution of the present invention) was prepared.

As a control, a substrate solution of a commercially available reagent was used.

A buffer solution was also prepared.

[1] Preparation of the Substrate Solution for Measuring Lipase Activity of the Present Invention (1) A portion (0.045 g) of the substrate for measuring lipase activity of the present invention; i.e., 12-o-dilauryl-rac-glycero-3-glutaric acid (6'-methylresorufin) ester (DGGMR) (the distributor Roche Diagnostics K. K. (Japan)), was fractionated into a beaker (volume: 10 mL).

(2) Subsequently, a portion (0.6 g) of the side-chain-type nonreactive modified silicone oil (polyether modified type); KF-355A (the distributor: Shin-Etsu Chemical Co., Ltd. (Japan)), was fractionated and added to the beaker of (1).

(3) After the addition (2) above, the content of the beaker was stirred at 67° C. to mix the substrate for measuring lipase activity (DGGMR) and the present modified silicone oil (KF-355A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of 40 mM L-sodium tartrate buffer (pH 4.0 at 20° C.)" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of 40 mM L-sodium tartrate buffer (pH 4.0 at 20° C.)" was mixed with (all) the "mixture prepared by mixing the substrate for measuring lipase activity (DGGMR) and the present modified silicone oil."

Stirring was carried out by mounting the beaker on a multi-stirrer (the model: M-3; the distributor AS ONE Corporation (Japan)) and rotating a magnet bar in the beaker while setting the dial of a control unit of the multi-stirrer at "3."

(5) Subsequently, a certain quantity of 40 mM L-sodium tartrate buffer (pH 4.0 at 20° C.) was further added to the "mixed liquid prepared by mixing the mixture (i.e., the mixture of the substrate for measuring lipase activity (DGGMR) and the present modified silicone oil) and a certain quantity of 40 mM L-sodium tartrate buffer (pH 4.0 at 20° C.)" of (4) above, so as to bring the final volume to 200 ml.

(6) Through the procedure described above, the substrate solution for measuring lipase activity of the present invention (the substrate for measuring lipase activity: DGGMR; the present modified silicone oil: KF-355A) was prepared.

In the substrate solution for measuring lipase activity, the concentration of the substrate for measuring lipase activity (DGGMR) was 0.3 mM, and that of the present modified silicone oil (KF-355A) was 0.3% (w/v).

In addition, neither concentration gradient nor strong turbidity was observed in the substrate solution for measuring lipase activity. It was visually confirmed that the substrate solution was uniformly mixed.

[2] Commercially Available Control Reagent

A commercially available reagent for measuring lipase activity (a reagent kit for measuring lipase activity); that is, Liquitech Lipase Color II (the distributor: Roche Diagnostics K. K. (Japan)), was used as a control reagent.

The "Liquitech Lipase Color II" (hereafter, it is occasionally referred to as a "commercially available control reagent") comprises a first reagent (i.e., a buffer) and a second reagent (i.e., a substrate solution) (it comprises DGGMR as a substrate for measuring lipase activity at 0.27 mM).

A "substrate solution" of the "commercially available control reagent" was used in this example.

[3] Preparation of Buffer Solution

The reagent component below was dissolved at designated concentration in pure water, and the pit level was adjusted to 8.4 (20° C.) to prepare the buffer solution.

Bicine (a buffer) 40 mM

2. Storage of Reagent (1) The substrate solution for measuring lipase activity of the present invention prepared in 1 [1] above was stored at 10'C in the dark for 390 days.

(2) The substrate solution of the commercially available control reagent prepared in 1 [2] above was stored at 5° C. in the dark for 300 days.

3. Measurement of the Amount of Substrate Degradation (1) The buffer of the day on which it was produced in 1 [3] above designated as the first reagent and the substrate solution for measuring lipase activity of the present invention stored at 10° C. (in the dark) in 2 (1) above designated as the second reagent were subjected to the measurement described below.

The measurement was carried out on the day of initiation of storage of the substrate solution for measuring lipase activity of the present invention (Day 0), 90 days after the initiation of storage, 180 days after the initiation of storage, 270 days after the initiation of storage, 360 days after the initiation of storage, and 390 days after the initiation of storage with the use of the substrate solution for measuring lipase activity of the present invention stored for the designated period of time.

At the outset, 960 μL of the second reagent was added to 1,600 μl of the first reagent to prepare a mixed liquid.

(2) Subsequently, the absorbance of the mixed liquid obtained in (1) above was measured at 580 nm with the use of the DU-7500 series spectrophotometer (the distributor: Beckman Coulter, Inc. (Japan)).

(3) Subsequently, the absorbance of the buffer of the day on which it was produced in 1 [3] above was measured at 580 nm as a blank test with the use of the DU-7500 series spectrophotometer (the distributor Beckman Coulter, Inc. (Japan)).

(4) Subsequently, the difference in the absorbance was determined by subtracting the absorbance measured in (3) above (i.e., a blank value) from the absorbance measured in (2) above.

(5) Subsequently, the difference in the absorbance determined in (4) above was divided by the molar absorption coefficient of 6'-methylresorufin at 580 nm (i.e., 60.65 (represented in cm×μmol$^{-1}$)), so as to calculate the concentration of 6'-methylresorufin generated upon DGGMR degradation during storage (represented in mM).

(6) Subsequently, the concentration of 6'-methylresorufin (represented in mM) generated upon degradation during storage determined in (5) above was divided by the concentration of DGGMR (0.3 mM) of the substrate solution for measuring lipase activity of the present invention of 1 [1] above, so as to calculate the ratio of the concentration of 6'-methylresorufin generated relative to the concentration of DGGMR (1 mM) (represented in %).

Specifically, "the ratio of DGGMR degraded during storage of the reagent relative to the concentration of DGGMR (1 mM) in the reagent" (i.e., the ratio of DGGMR degradation) was calculated (represented in %).

(7) The procedures described in (1) to (6) above were performed in the same manner, except that the substrate solution for measuring lipase activity of the present invention as the second reagent in (1) above was replaced with the substrate solution of the commercially available control reagent stored at 5° C. (in the dark) for 300 days in 2 (2) above, the measurement in (1) was carried out on the day of initiation of storage (Day 0), 90 days after the initiation of storage, 150 days after the initiation of storage, and 300 days after the initiation of storage, and the concentration of DGGMR (0.3 mM) in the substrate solution for measuring lipase activity of the present invention of (6) above was replaced with the concentration of DGGMR (0.27 mM) in the substrate solution of the commercially available control reagent of 1 [2] above, so as to calculate the ratio of the concentration of 6'-methylresorufin generated relative to the concentration of DGGMR (1 mM) when the substrate solution of the commercially available control reagent of 2 (2) above was used as the second reagent (represented in %).

Specifically, "the ratio of DGGMR degraded during storage of the reagent relative to the concentration of DGGMR (1 mM) in the reagent" (i.e., the ratio of DGGMR degradation) was calculated (represented in %).

4. Results of Measurement

Figure 6:
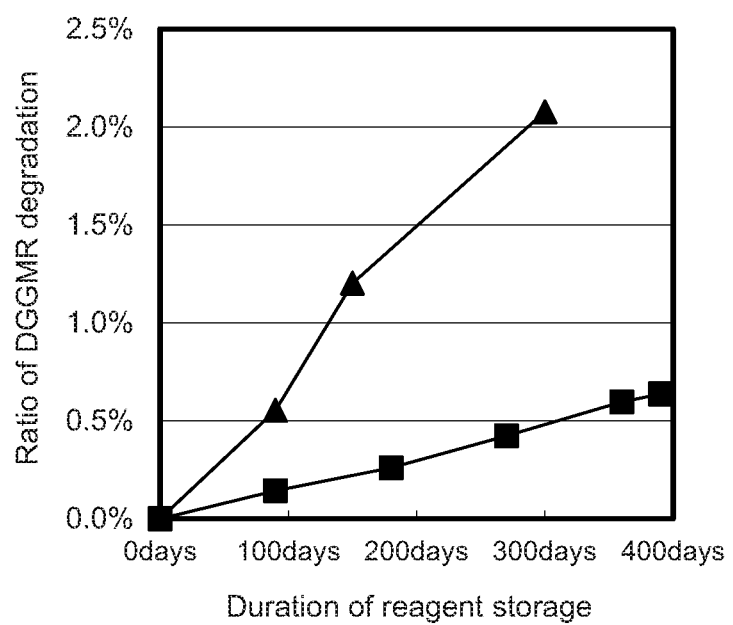
FIG. 6 shows the percentage of DGGMR degraded at the time of storage of the substrate solution for measuring lipase activity of the present invention and a substrate solution of a commercially available control reagent.

Table 4 and FIG. 6 show "the ratio of DGGMR degraded during storage of the reagent relative to the concentration of DGGMR (1 mM) in the reagent" (i.e., the ratio of DGGMR degradation) (represented in %) when the substrate solution for measuring lipase activity of the present invention of 2 (1) above was used as the second reagent, which was determined in 3 above.

Table 4 and FIG. 6 also show "the ratio of DGGMR degraded during storage of the reagent relative to the concentration of DGGMR (1 mM) in the reagent" (i.e., the ratio of DGGMR degradation) (represented in %) when the substrate solution of the commercially available control reagent of 2 (2) above was used as the second reagent, which was determined in 3 above.

Table 4 and FIG. 6 each show "the ratio of DGGMR degradation" determined over time relative to "the ratio of DGGMR degradation" designated as "0" on the day of initiation of storage (Day 0).

In FIG. 6, the horizontal axis indicates the duration of reagent storage (represented in the number of days), and the vertical axis indicates the ratio of DGGMR degradation (represented in %).

In FIG. 6, "the ratio of DGGMR degradation" of the substrate solution for measuring lipase activity of the present invention is represented by the symbol "■" and "the ratio of DGGMR degradation" of the substrate solution of the commercially available control reagent is represented by the symbol "▲."

TABLE 4

| Duration of reagent storage | Ratio of DGGMR degradation Substrate solution for measuring lipase activity of the invention |
|---|---|
| 0 days | 0.0% |
| 90 days | 0.1% |
| 180 days | 0.3% |
| 270 days | 0.4% |
| 360 days | 0.6% |
| 390 days | 0.6% |

| Duration of reagent storage | Ratio of DGGMR degradation Substrate solution of commercially available control reagent |
|---|---|
| 0 days | 0.0% |
| 90 days | 0.6% |
| 150 days | 1.2% |
| 300 days | 2.1% |

5. Discussion (1) Table 4 and FIG. 6 demonstrate that, as a result of storage at 10° C. for 390 days, "the ratio of DGGMR degradation" of the substrate solution for measuring lipase activity of the present invention is 0.6%

Table 4 and FIG. 6 also demonstrate that, as a result of storage at 5° C. for 300 days. "the ratio of DGGMR degradation" of the substrate solution of the commercially available control reagent is 2.1%.

Specifically, "the ratio of DGGMR degradation" of the substrate solution for measuring lipase activity of the present invention is significantly lower than "the ratio of DGGMR degradation" of the substrate solution of the commercially available control reagent.

(2) On the basis of the results attained as a result of refrigeration in this example, accordingly, the present invention was found to be capable of effectively suppressing DGGMR degradation, excellent in storage stability, and capable of accurate measurement over a long period of time.

[Example 6] (Verification of the Effects of the Substrate Solution for Measuring Lipase Activity of the Present Invention-6)

The effects of the substrate solution for measuring lipase activity of the present invention concerning storage stability were reexamined.

1. Reagent

In total, three lots of the substrate solutions for measuring lipase activity of the present invention (i.e., the substrate solutions for measuring lipase activity comprising the emulsion solution of the present invention) were prepared.

(1) A portion (0.045 g) of the substrate for measuring lipase activity of the present invention; i.e., 1,2-o-dilauryl-rac-glycero-3-glutaric acid (6'-methylresorufin) ester (DG-GMR) (the distributor: Roche Diagnostics K. K. (Japan)), was fractionated into a beaker (volume: 10 mL).

(2) Subsequently, a portion (0.6 g) of the side-chain-type nonreactive modified silicone oil (polyether modified type); KF-355A (the distributor: Shin-Etsu Chemical Co., Ltd. (Japan)), was fractionated and added to the beaker of (1).

(3) After the addition (2) above, the content of the beaker was stirred at 67° C. to mix the substrate for measuring lipase activity (DGGMR) and the present modified silicone oil (KF-355A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor AS ONE Corporation (Japan)) and rotating a magnet bar in the beaker while setting the dial of a control unit of the multi-stirrer at "3."

(4) Subsequently, a "certain quantity (4.0 mL) of 40 mM L-sodium tartrate buffer (pH 4.0 at 20° C.)" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of 40 mM L-sodium tartrate buffer (pH 4.0 at 20° C.)" was mixed with (all) the "mixture prepared by mixing the substrate for measuring lipase activity (DG-GMR) and the present modified silicone oil."

Stirring was carried out by mounting the beaker on a multi-stirrer (the model: M-3; the distributor AS ONE Corporation (Japan)) and rotating a magnet bar in the beaker while setting the dial of a control unit of the multi-stirrer at "3."

(5) Subsequently, a certain quantity of 40 mM L-sodium tartrate buffer (pH 4.0 at 20° C.) was further added to the "mixed liquid prepared by mixing the mixture (i.e., the mixture of the substrate for measuring lipase activity (DG-GMR) and the present modified silicone oil) and a certain quantity of 40 mM L-sodium tartrate buffer (pH 4.0 at 20° ° C.)" of (4) above, so as to bring the final volume to 200 ml.

(6) Through the procedure described above, the substrate solution for measuring lipase activity of the present invention (the substrate for measuring lipase activity: DGGMR; the present modified silicone oil: KF-355A) was prepared.

The resultant was designated as the first lot.

(7) The procedures described in (1) to (6) above were repeated two times to separately prepare the substrate solutions for measuring lipase activity of the present invention (the substrate for measuring lipase activity: DGGMR; the present modified silicone oil: KF-355A).

The resultants were designated as the second lot and the third lot, respectively.

(8) In all of the first lot, the second lot, and the third lot of the substrate solutions for measuring lipase activity of the present invention prepared in (1) to (7) above, the concentration of the substrate for measuring lipase activity (DG-GMR) was 0.3 mM, and that of the present modified silicone oil (KF-355A) was 0.3% (w/v).

In addition, neither concentration gradient nor strong turbidity was observed in these substrate solutions for measuring lipase activity. It was visually confirmed that the substrate solutions were uniformly mixed.

2. Storage of Reagent

The first lot, the second lot, and the third lot of the substrate solutions for measuring lipase activity of the present invention prepared in 1 above were separately stored at 10° ° C. in the dark for 16 months.

3. Measurement of Diameter of Micelles in the Emulsion of the Substrate Solution for Measuring Lipase Activity of the Present Invention The first lot, the second lot, and the third lot of the substrate solutions for measuring lipase activity of the present invention stored in 2 above were subjected to measurement of diameters of micelles in the emulsions thereof.

The measurement was carried out on the day of initiation of storage of the substrate solution for measuring lipase activity of the present invention (Day 0) and 16 months after the initiation of storage with the use of the substrate solution for measuring lipase activity of the present invention stored for the designated period of time.

(1) The first lot, the second lot, and the third lot of the substrate solutions for measuring lipase activity of the present invention stored at 10° C. (in the dark) for 16 months in 2 above were introduced into separate plastic cells in amounts of 2 ml each.

(2) Subsequently, an optical probe (optical fiber) of a dynamic light-scattering particle size distribution analyzer (the model: Nanotrac UPA-EX250; the distributor. Nikkiso Co., Ltd. (Japan)) was inserted into each plastic cell one by one. The diameters (particle sizes) of micelles in an emulsion of each of the first lot, the second lot, and the third lot of the substrate solutions for measuring lipase activity of the present invention in each plastic cell were measured. The measurement was carried out at room temperature (25° C.).

4. Results of Measurement

Figure 7:
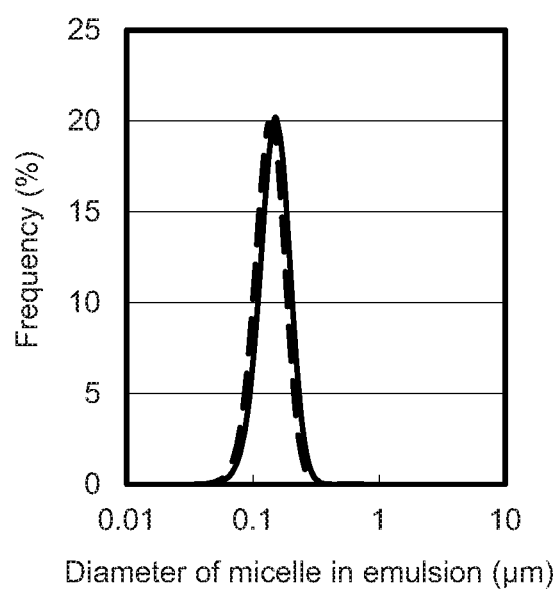
FIG. 7 shows the distribution of the diameter of micelles (particle size) in an emulsion of the stored substrate solution for measuring lipase activity of the present invention.
Figure 8:
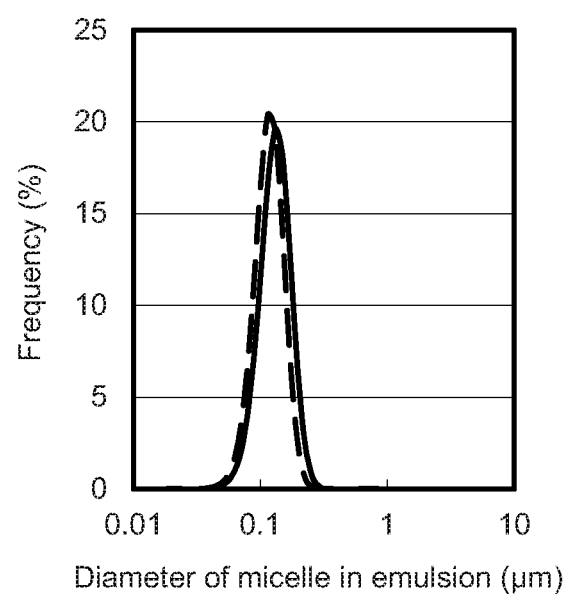
FIG. 8 shows the distribution of the diameter of micelles (particle size) in an emulsion of the stored substrate solution for measuring lipase activity of the present invention.
Figure 9:
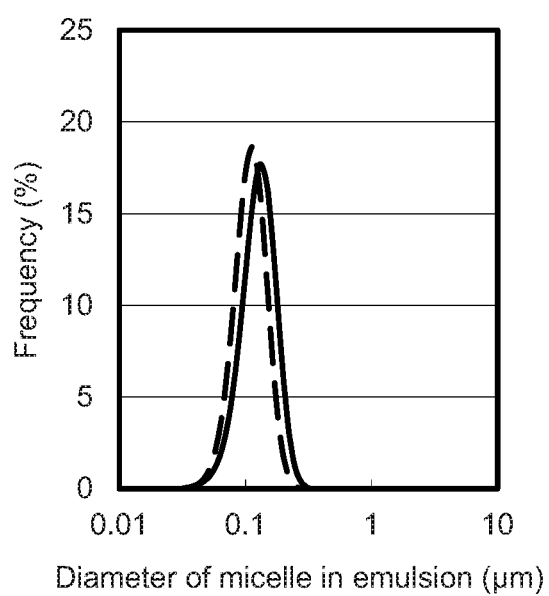
FIG. 9 shows the distribution of the diameter of micelles (particle size) in an emulsion of the stored substrate solution for measuring lipase activity of the present invention.

FIG. 7 shows the distribution of the diameters (particle sizes) of micelles in an emulsion of the first lot of the substrate solution for measuring lipase activity of the present invention measured in 3 above, FIG. 8 shows the distribution of the diameters (particle sizes) of micelles in an emulsion of the second lot of the substrate solution for measuring lipase activity of the present invention, and FIG. 9 shows the distribution of the diameters (particle sizes) of micelles in an emulsion of the third lot of the substrate solution for measuring lipase activity of the present invention.

FIG. 7, FIG. 8, and FIG. 9 show the average diameter (particle size) of micelles in an emulsion of the substrate solution for measuring lipase activity of the present invention.

In FIG. 7, FIG. 8, and FIG. 9, the horizontal axis indicates the diameter (particle size) of micelles in an emulsion (the average, represented in μm) and the vertical axis indicates the frequency (represented in %).

In FIG. 7, FIG. 8, and FIG. 9, a broken line represents the results of measurement on the day of initiation of storage (Day 0) and a solid line represents the results of measurement 16 months after the initiation of storage.

5. Discussion

FIG. 7, FIG. 8, and FIG. 9 demonstrate that the distribution of the diameters (particle sizes) of micelles in emulsions of any of the first lot, the second lot, and the third lot of the substrate solutions for measuring lipase activity of the present invention is within a range of 100 nm to 200 nm (0.1 μm to 0.2 μm) and in the vicinity thereof on the basis of the results of measurements attained on the day of initiation of storage (Day 0) and 16 months after the initiation of storage.

FIG. 7, FIG. 8, and FIG. 9 also demonstrate that the distribution of the diameters (particle sizes) of micelles in emulsions of any of the first lot, the second lot, and the third lot of the substrate solutions for measuring lipase activity of the present invention determined on the day of initiation of storage (Day 0) is substantially the same as that determined 16 months after the initiation of storage.

As described above, the diameter (particle size) of micelles in an emulsion of the substrate solution for measuring lipase activity of the present invention was found to be within a range of 80 nm to 600 nm, so that the reaction rate with the lipase is high, an emulsion is stable, and a substrate solution for measuring lipase activity can be stored and used for a long period of time. It was actually confirmed that the distribution of the diameters (particle sizes) of micelles in an emulsion was maintained stable over a long period of time (i.e., for 16 months).

[Example 7] (Verification of Effects of the Reagent for Measuring Lipase Activity of the Present Invention)

The effects of the reagent for measuring lipase activity of the present invention concerning storage stability (the reagent comprising the substrate solution for measuring lipase activity of the present invention) were examined.

1. The Reagent for Measuring Lipase Activity of the Present Invention

The first reagent and the second reagent for measuring lipase activity of the present invention were prepared.

[1] First Reagent

The reagent components below were dissolved at designated concentration in pure water, and the pH level was adjusted to 8.4 (20° C.) to prepare the first reagent for measuring lipase activity of the present invention.

Sodium deoxycholate (a lipase promoter) 2% (w/v)
Calcium chloride (a lipase activator) 20 mM
Colipase (porcine pancrease-derived; the distributor: Roche Diagnostics K. K. (Japan)) 750K Unit/L (10 mg/L)
Bicine (a buffer) 80 mM The first reagent was prepared separately (three times in total), and the resultants were designated as the first lot, the second lot, and the third lot of the first reagents of the reagents for measuring lipase activity of the present invention.

[2] Second Reagent

In total, three lots of the second reagents of the reagents for measuring lipase activity of the present invention were prepared.

(1) A portion (0.045 g) of the substrate for measuring lipase activity of the present invention; i.e., 1,2-o-dilauryl-rac-glycero-3-glutaric acid (6'-methylresorufin) ester (DG-GMR) (the distributor: Roche Diagnostics K. K. (Japan)), was fractionated into a beaker (volume: 10 mL).

(2) Subsequently, a portion (0.6 g) of the side-chain-type nonreactive modified silicone oil (polyether modified type); KF-355A (the distributor: Shin-Etsu Chemical Co., Ltd. (Japan)), was fractionated and added to the beaker of (1).

(3) After the addition (2) above, the content of the beaker was stirred at 67° C. to mix the substrate for measuring lipase activity (DGGMR) and the present modified silicone oil (KF-355A) in the beaker.

This process of mixing (stirring) was performed for 5 minutes to prepare a "mixture of the substrate for measuring lipase activity (DGGMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(4) Subsequently, a "certain quantity (4.0 mL) of 40 mM L-sodium tartrate buffer (pH 4.0 at 20° C.)" was added to (all) the "mixture of the substrate for measuring lipase activity (DGGMR) and the present modified silicone oil" in the beaker of (3) with stirring at room temperature (25° C.) with the use of a micropipette.

After the addition, stirring was continued at room temperature (25° C.) for 5 minutes. In this way, the "certain quantity (4.0 mL) of 40 mM L-sodium tartrate buffer (pH 4.0 at 20° C.)" was mixed with (all) the "mixture prepared by mixing the substrate for measuring lipase activity (DG-GMR) and the present modified silicone oil."

Stirring was carried out by mounting the beaker on a multi-stirrer (the model: M-3; the distributor: AS ONE Corporation (Japan)) and rotating a magnet bar in the beaker while setting the dial of a control unit of the multi-stirrer at "3."

(5) Subsequently, a certain quantity of 40 mM L-sodium tartrate buffer (pH 4.0 at 20° C.) was further added to the "mixed liquid prepared by mixing the mixture (i.e., the mixture of the substrate for measuring lipase activity (DG-GMR) and the present modified silicone oil) and a certain quantity of 40 mM L-sodium tartrate buffer (pH 4.0 at 20° C.)" of (4) above, so as to bring the final volume to 200 ml.

(6) Through the procedure described above, the substrate solution for measuring lipase activity of the present invention (the substrate for measuring lipase activity: DGGMR; the present modified silicone oil: KF-355A) was prepared.

The resultant was designated as the first lot of the second reagent for measuring lipase activity of the present invention.

(7) The procedures described in (1) to (6) above were repeated two times to separately prepare the substrate solutions fir measuring lipase activity of the present invention (the substrate for measuring lipase activity: DGGMR; the present modified silicone oil: KF-355A).

The resultants were designated as the second lot and the third lot of the second reagents for measuring lipase activity of the present invention, respectively.

(8) In all of the first lot, the second lot, and the third lot of the substrate solutions for measuring lipase activity of the present invention prepared in (1) to (7) above, the concentration of the substrate for measuring lipase activity (DG-GMR) was 0.3 mM, and that of the present modified silicone oil (KF-355A) was 0.3% (w/v).

In addition, neither concentration gradient nor strong turbidity was observed in these substrate solutions for measuring lipase activity. It was visually confirmed that the substrate solutions were uniformly mixed.

2. Storage of Reagent (1) The first lot, the second lot, and the third lot of the first reagents for measuring lipase activity of the present invention prepared in 1 [1] above were separately stored at 10° C. in the dark for 13 months.

(2) The first lot, the second lot, and the third lot of the second reagents for measuring lipase activity of the present invention prepared in 1 [2] above were stored at 10° C. in the dark for 13 months.

3. Sample

The following "(1) control serum-1," "(2) control serum-2," and "(3) control serum-3" were used as samples.

(1) Control Serum-1

A commercially available control serum for quality control (i.e., Aalto Control LM; the distributor Shino-Test Corporation (Japan)) was mixed with the same amount of a "prototype" of a control serum for quality control (i.e., Aalto Control II; the distributor. Shino-Test Corporation (Japan)). The resulting mixture was used as the "control serum-1."

(2) Control Serum-2

A "prototype" of a control serum for quality control (i.e., Aalto Control II; Shino-Test Corporation (Japan)) was used as the "control serum-2."

(3) Control Serum-3

A commercially available control serum for quality control "QAP troll 2×" (the production number: QL-215; the distributor: Sysmex Corporation (Japan)) was used as the "control serum-3."

4. Measurement of Lipase Activity in a Sample

With the use of the first reagent and the second reagent for measuring lipase activity of the present invention stored at 10° C. (in the dark) for 13 months in 2 above, lipase activity in the samples of 3 above was measured using a 7180 clinical analyzer (the distributor: Hitachi High-Technologies Corporation (Japan)).

The measurement was carried out on the day of initiation of storage of the first reagent and the second reagent for measuring lipase activity of the present invention (Day 0), 3 months after the initiation of storage, 6 months after the initiation of storage, 9 months after the initiation of storage, 12 months after the initiation of storage, and 13 months after the initiation of storage with the use of the first reagent and the second reagent for measuring lipase activity of the present invention stored for the designated period of time.

(1) In the 7180 clinical analyzer, 160 µL of the first lot of "the first reagent" stored in 2 (1) above was added as the first reagent to 2.6 µL each of the samples described in 3 above (i.e., (1) control serum-1, (2) control serum-2, and (3) control serum-3), and the reaction was allowed to proceed at 37° C.

(2) Subsequently, between point 16 (270.093 seconds after addition of the first reagent) and point 17 (286.977 seconds after addition of the first reagent), 96 µl of the first lot of the "second reagent" stored in 2 (2) above was added as the second reagent, and the reaction was allowed to proceed at 37° C.

(3) Subsequently, a change in the absorbance from point 20 (340.510 seconds after addition of the first reagent) and point 24 (411.887 seconds after addition of the first reagent) was measured at a main wavelength of 570 nm and another wavelength of 700 nm (a change in the absorbance was measured based on an increase in the concentration of 6'-methylresorufin generated in response to lipase activity value in a sample).

(4) As a calibrator for calibration, a "calibrator II (C.f.a.s. II) for automated analysis" (Lot No. 167255-01; the distributor: Roche Diagnostics K. K. (Japan)) was used.

The procedures (1) to (3) described above were performed in the same manner, except that this "calibrator II (C.f.a.s. II) for automated analysis" was used as a sample. A change in the absorbance when the calibrator "calibrator II (C.f.a.s. II) for automated analysis" was used for measurement was determined (a change in the absorbance was measured based on an increase in the concentration of 6'-methylresorufin generated in response to lipase activity value (known value) in the calibrator).

(5) Physiological Saline was Used for Measurement of a Blank Reagent.

The procedures (1) to (3) described above were performed in the same manner, except that physiological saline was used as a sample, and a change in the absorbance when physiological saline was measured was determined (a change in the absorbance of the blank reagent was measured).

(6) Subsequently, a "difference in a change in the absorbance of the sample" was calculated by subtracting the change in the absorbance of the blank reagent between the above points calculated in (5) above from the change in the absorbance of each sample of 3 above between the above points calculated in (3) above.

In addition, a "difference in a change in the absorbance of the calibrator" was calculated by subtracting the change in the absorbance of the blank reagent between the above points calculated in (5) above from the change in the absorbance of the calibrator (with a known lipase activity value) between the above points calculated in (4) above.

Subsequently, the "difference in the change in the absorbance of the sample," the "difference in the change in the absorbance of the calibrator," and the known "lipase activity value of the calibrator" were compared. The proportion was then calculated to determine the lipase activity value of each sample as described in 3 above.

(7) The procedures described in (1) to (6) described above were performed in the same manner, except that the first lot of the "first reagent" stored in 2 (1) above as the first reagent in (1) above was replaced with the second lot and the first lot of the "second reagent" stored in 2 (2) above as the second reagent of (2) was replaced with the second lot. The lipase activity value of each sample of 3 above when the second lot of the first reagent was used and the second lot of the second reagent was used was determined.

(8) Also, the procedures (1) to (6) described above were performed in the same manner, except that the first lot of the "first reagent" stored in 2 (1) above as the first reagent in (1) above was replaced with the third lot and the first lot of the "second reagent" stored in 2 (2) above as the second reagent of (2) was replaced with the third lot. The lipase activity value of each sample of 3 above when the third lot of the first reagent was used and the third lot of the second reagent was used was determined.

5. Results of Measurement

Table 5 shows the lipase activity value of each sample of 3 above measured in 4 above.

In Table 5, the unit of the measured value (the lipase activity value of each sample) is represented in Unit/L.

In Table 5, a numerical value in parentheses represents a value calculated by dividing the measured value (the lipase activity value) by the measured value (the lipase activity value) of each sample on the day of initiation of storage (Day 0) in percentage.

Figure 10:
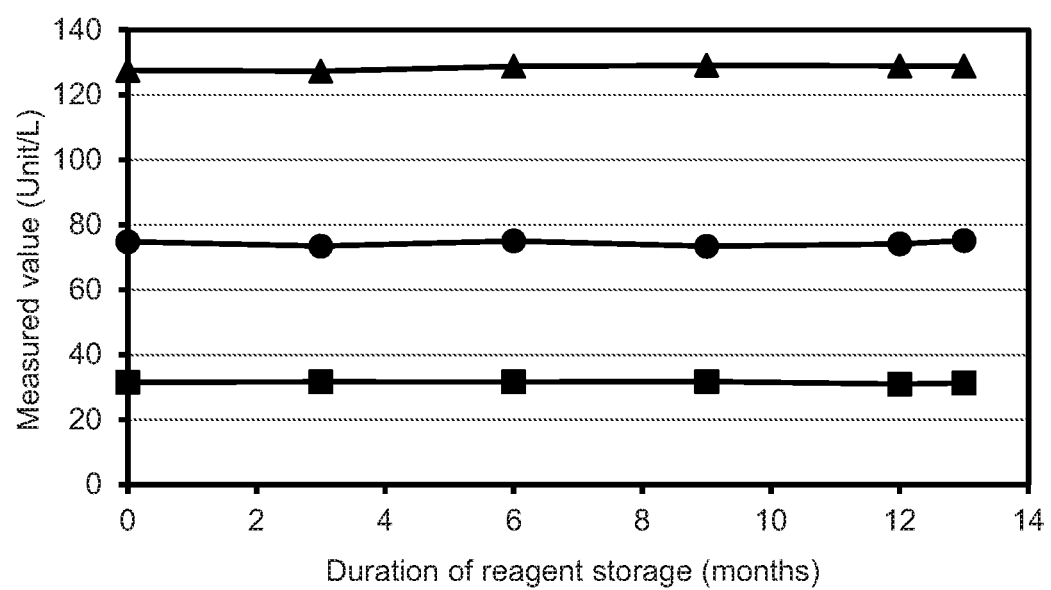
FIG. 10 shows the results of measuring lipase activity in a sample using the stored reagent for measuring lipase activity of the present invention.

FIG. 10 shows the lipase activity value of each sample of 3 above determined with the use of the first lot of the first reagent and the first lot of the second reagent in 4 above.

Figure 11:
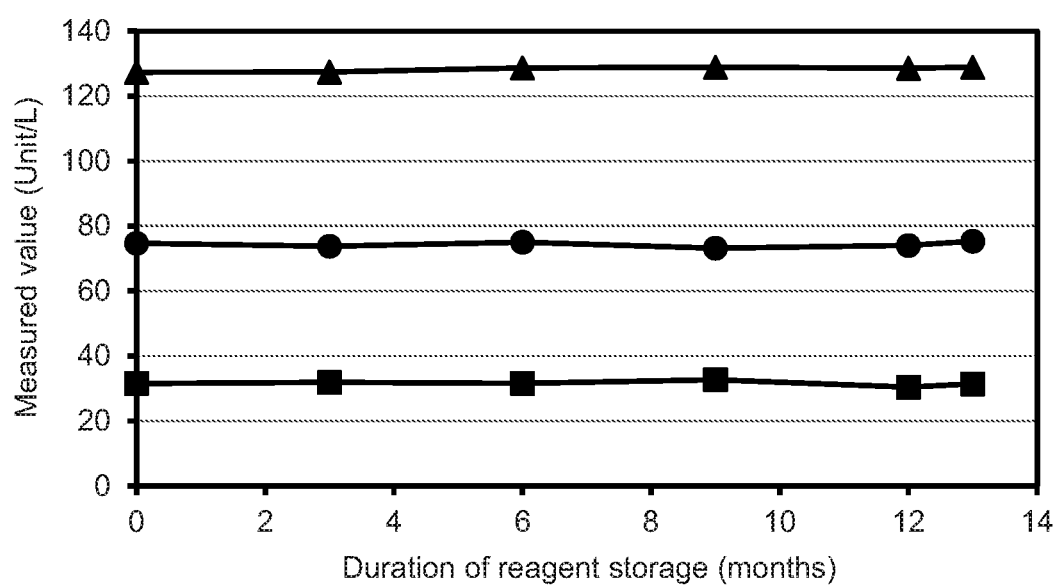
FIG. 11 shows the results of measuring lipase activity in a sample using the stored reagent for measuring lipase activity of the present invention.

FIG. 11 shows the lipase activity value of each sample of 3 above determined with the use of the second lot of the first reagent and the second lot of the second reagent in 4 above.

Figure 12:
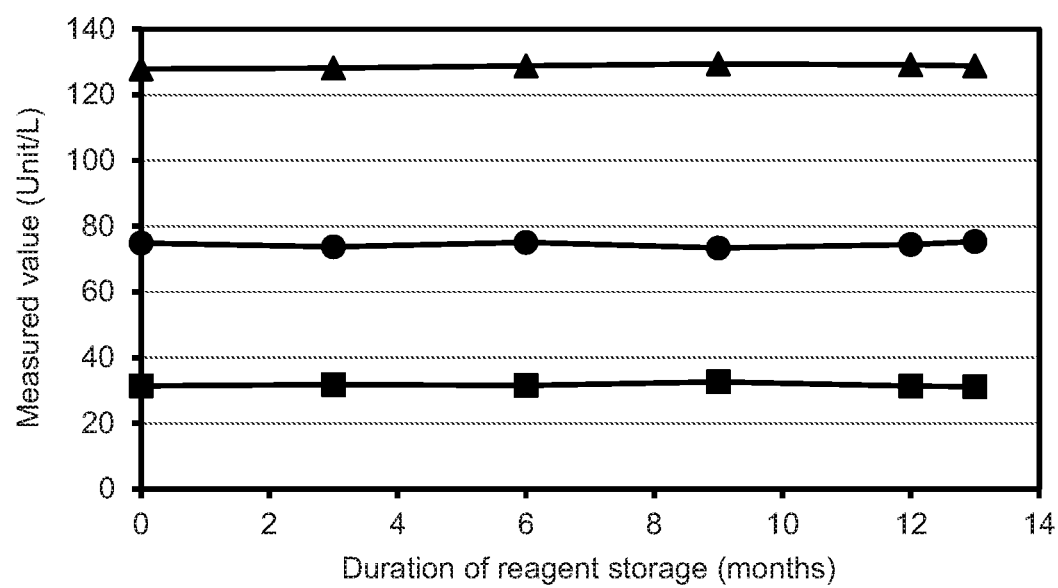
FIG. 12 shows the results of measuring lipase activity in a sample using the stored reagent for measuring lipase activity of the present invention.

FIG. 12 shows the lipase activity value of each sample of 3 above determined with the use of the third lot of the first reagent and the third lot of the second reagent in 4 above.

In FIG. 10, FIG. 11, and FIG. 12, the horizontal axis indicates the duration of reagent storage (represented in the number of months) and the vertical axis indicates the measured value (the lipase activity value of each sample) (represented in Unit/L).

In FIG. 10, FIG. 11, and FIG. 12, the measured value is represented by the symbol "●" when the sample is "(1) control serum-1," the measured value is represented by the symbol "▲" when the sample is "(2) control serum-2," and the measured value is represented by the symbol "■" when the sample is "(3) control serum-3."

TABLE 5

| Duration of reagent | Measured value (Lipase activity value of sample) First reagent/Second reagent: First lot | | |
|---|---|---|---|
| storage | Control serum-1 | Control serum-2 | Control serum-3 |
| Initiation of storage | 74.8 [100%] | 127.5 [100%] | 31.5 [100%] |
| 3 months | 73.4 (98%) | 127.3 (100%) | 31.7 (101%) |
| 6 months | 75.0 (100%) | 128.8 (101%) | 31.6 (100%) |
| 9 months | 73.4 (98%) | 129.1 (101%) | 31.7 (101%) |
| 12 months | 74.1 (99%) | 128.9 (101%) | 30.9 (98%) |
| 13 months | 75.1 (100%) | 128.7 (101%) | 31.3 (99%) |

TABLE 5-continued

| Duration of reagent | Measured value (Lipase activity value of sample) First reagent/Second reagent: Second lot | | |
|---|---|---|---|
| storage | Control serum-1 | Control serum-2 | Control serum-3 |
| Initiation of storage | 74.7 [100%] | 127.3 [100%] | 31.5 [100%] |
| 3 months | 73.8 (99%) | 127.4 (100%) | 31.9 (101%) |
| 6 months | 75.0 (100%) | 128.7 (101%) | 31.6 (100%) |
| 9 months | 73.2 (98%) | 128.9 (101%) | 32.7 (104%) |
| 12 months | 74.0 (99%) | 128.5 (101%) | 30.4 (97%) |
| 13 months | 75.3 (101%) | 128.9 (101%) | 31.4 (100%) |

| Duration of reagent | Measured value (Lipase activity value of sample) First reagent/Second reagent: Third lot | | |
|---|---|---|---|
| storage | Control serum-1 | Control serum-2 | Control serum-3 |
| Initiation of storage | 74.9 [100%] | 127.9 [100%] | 31.4 [100%] |
| 3 months | 73.7 (98%) | 128.1 (100%) | 31.8 (101%) |
| 6 months | 75.1 (100%) | 128.8 (101%) | 31.5 (100%) |
| 9 months | 73.4 (98%) | 129.4 (101%) | 32.6 (104%) |
| 12 months | 74.4 (99%) | 129.1 (101%) | 31.3 (100%) |
| 13 months | 75.3 (101%) | 128.8 (101%) | 31.1 (99%) |

[Unit of measured value: Unit/L]

6. Discussion (1) Table 5 and FIG. 10 demonstrate that, when the first lot of the first reagent and the first lot of the second reagent for measuring lipase activity of the present invention are used, the measured value during the reagent storage is 98% to 100% in the case of "(1) control serum-1," it is 100% to 101% in the case of "(2) control serum-2," and it is 98% to 101% in the case of "(3) control serum-3," relative to the measured value (the lipase activity value) on the day of initiation of storage (Day 0).

(2) Table 5 and FIG. 11 demonstrate that, when the second lot of the first reagent and the second lot of the second reagent for measuring lipase activity of the present invention are used, the measured value during the reagent storage is 98% to 101% in the case of "(1) control serum-1," it is 100% to 101% in the case of "(2) control scrum-2," and it is 97% to 104% in the case of "(3) control serum-3," relative to the measured value (the lipase activity value) on the day of initiation of storage (Day 0).

(3) Further, Table 5 and FIG. 12 demonstrate that, when the third lot of the first reagent and the third lot of the second reagent for measuring lipase activity of the present invention are used, the measured value during the reagent storage is 98% to 101% in the case of "(1) control serum-1," it is 100% to 101% in the case of "(2) control serum-2," and it is 99'/o to 104% in the case of "(3) control serum-3," relative to the measured value (the lipase activity value) on the day of initiation of storage (Day 0).

(4) That is, Table 5, FIG. 10, FIG. 11, and FIG. 12 demonstrate that the measured value (the lipase activity value) 13 months after the initiation of storage (at 10° C. in the dark) is substantially the same as the measured value (the lipase activity value) on the day of initiation of storage (Day 0) in any of the first lot, the second lot, and the third lot of the first reagents and the second reagents for measuring lipase activity of the present invention.

More specifically, the capacity of the reagent for measuring lipase activity of the present invention is maintained stable for a long period of time (i.e., for 13 months).

(5) On the basis of the results examined in this example, accordingly, the present invention was confirmed to be excellent in storage stability and capable of accurate measurement over a long period of time.

We claim:

1. An emulsion comprising micelle particles of 1,2-o-dilauryl-rac-glycero-3-glutaric acid (6'-methylresorufin) ester and side-chain-type nonreactive polyether-modified-type modified silicone oil.

2. A substrate for measuring lipase activity comprising the emulsion of claim 1.

3. A method for measuring lipase activity in an aqueous sample comprising:
   contacting the sample with the substrate of claim 2; and
   measuring an absorbance of the sample having the substrate at 580 nm to determine lipase activity in the sample.

4. A reagent for measuring lipase activity comprising the substrate of claim 2.

5. A method for stabilizing 1,2-o-dilauryl-rac-glycero-3-glutaric acid (6'-methylresorufin) ester as a substrate for measuring lipase activity comprising:
   (a) contacting a side-chain-type nonreactive polyether-modified-type modified silicone oil with 1,2-o-dilauryl-rac-glycero-3-glutaric acid (6'-methylresorufin) ester to prepare a mixture; and
   (b) mixing the mixture of step (a) with water or an aqueous solution to form an emulsion comprising micelle particles 1,2-o-dilauryl-rac-glycero-3-glutaric acid (6'-methylresorufin) ester and the side-chain-type nonreactive polyether-modified-type silicone oil.

* * * * *